United States Patent
Zobel et al.

(10) Patent No.: US 7,534,081 B2
(45) Date of Patent: May 19, 2009

(54) APPARATUS AND METHOD FOR TRANSFERRING SAMPLES FROM A SOURCE TO A TARGET

(75) Inventors: Hans-Jörg Zobel, New York, NY (US); Gerard William Leeman, Stoneham, MA (US); Amir Porat, Gany-Yehuda (IL); Moshe Gombinsky, Bat-Yam (IL)

(73) Assignee: Festo Corporation, Hauppauge, NY (US)

( * ) Notice: Subject to any disclaimer, the term of this patent is extended or adjusted under 35 U.S.C. 154(b) by 611 days.

(21) Appl. No.: 11/135,962

(22) Filed: May 24, 2005

(65) Prior Publication Data

US 2006/0269385 A1 Nov. 30, 2006

(51) Int. Cl.
*G01N 33/497* (2006.01)
(52) U.S. Cl. .................. 414/222.01; 210/695
(58) Field of Classification Search .......... 210/695; 414/222.01, 222.12
See application file for complete search history.

(56) References Cited

U.S. PATENT DOCUMENTS

| | | | |
|---|---|---|---|
| 4,292,920 A | 10/1981 | Smith et al. | |
| 5,055,263 A * | 10/1991 | Meltzer | 422/65 |
| 5,288,468 A | 2/1994 | Church et al. | |
| 5,443,791 A * | 8/1995 | Cathcart et al. | 422/65 |
| 5,647,994 A * | 7/1997 | Tuunanen et al. | 210/695 |
| 5,779,907 A | 7/1998 | Yu | |
| 5,882,930 A * | 3/1999 | Baier | 436/49 |
| 6,040,192 A | 3/2000 | Tuunanen | |
| 6,297,062 B1 | 10/2001 | Gombinski et al. | |
| 6,403,038 B1 * | 6/2002 | Heermann | 422/101 |
| 6,409,925 B1 | 6/2002 | Gombinsky et al. | |
| 6,672,458 B2 * | 1/2004 | Hansen et al. | 209/224 |
| 6,780,648 B1 | 8/2004 | Sun | |
| 6,942,806 B2 * | 9/2005 | Franzreb et al. | 210/695 |
| 2001/0055545 A1 | 12/2001 | Takii et al. | |
| 2005/0035143 A1 | 2/2005 | Massaro et al. | |
| 2005/0132822 A1 | 6/2005 | Massaro | |

FOREIGN PATENT DOCUMENTS

| | | |
|---|---|---|
| WO | WO 87/05536 | 9/1987 |
| WO | WO 94/18565 | 11/1994 |
| WO | WO 95/00247 | 1/1995 |
| WO | WO 96/09550 | 3/1996 |
| WO | WO 96/12959 | 5/1996 |
| WO | WO 99/40444 | 8/1999 |
| WO | WO 99/42832 | 11/1999 |
| WO | WO 02/49761 A2 | 6/2002 |

(Continued)

*Primary Examiner*—Charles Fox
(74) *Attorney, Agent, or Firm*—Hoffmann & Baron, LLP

(57) ABSTRACT

A control system for transferring a sample from a source vessel to a target vessel generally includes a vessel unit, a primary transfer unit, an x-drive, a y-drive, a z-drive and a control unit for controlling the drives. The vessel unit includes a support plate for supporting the source vessel and the target vessel thereon and the transfer unit includes at least one transfer device for transferring the sample from the source vessel to the target vessel. The x-, y- and z-drives reciprocally translate one of the support plate and the transfer device in a respective x-direction, y-direction and z-direction, wherein the x, y and z directions define a three axis Cartesian coordinate system.

26 Claims, 23 Drawing Sheets

FOREIGN PATENT DOCUMENTS

| WO | WO 03/085407 A1 | 10/2003 |
| WO | WO 03/090897 A1 | 11/2003 |
| WO | WO 2004/009238 A1 | 1/2004 |
| WO | WO 2004/009300 A1 | 1/2004 |
| WO | WO 2004/035217 | 4/2004 |
| WO | WO 2004/069413 A1 | 8/2004 |
| WO | WO 2005/065831 | 7/2005 |

\* cited by examiner

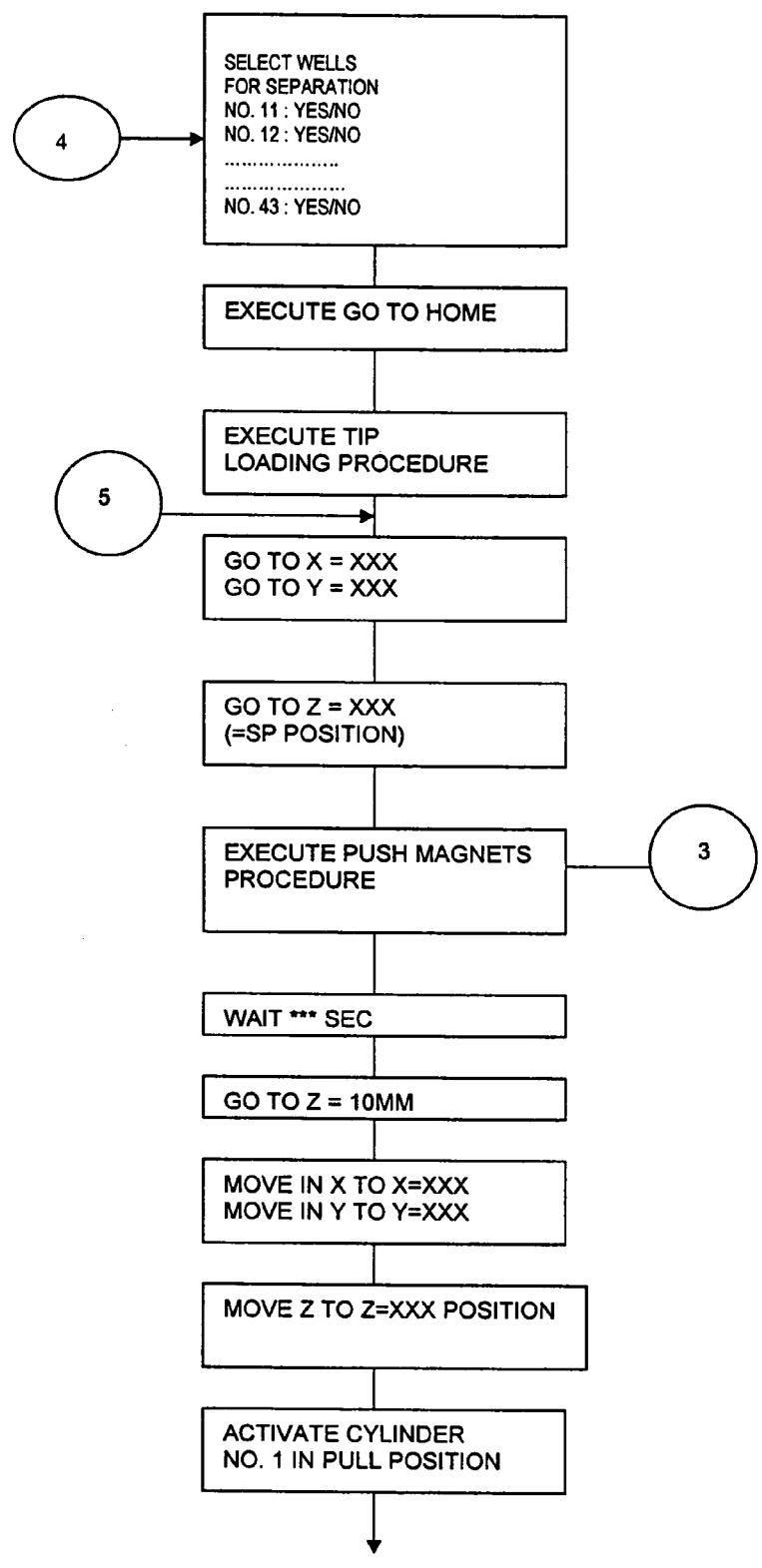
FIG. 12a  MAGNETIC SEPARATION PROCEDURE
SEE FIG. 12b

FIG. 12b

SEE FIG. 12a

SHAKE TIP? 
- YES → SET J=0 → MOVE Z=XXX → WAIT 2 SEC → MOVE Z IN -5MM → J=J+1 → J<5? YES loops back to MOVE Z=XXX; NO →
- NO ↓

APPLY FLIP FLOP?
- YES → OPERATE FLIP FLOP PROCEDURE →
- NO ↓

START ANOTHER SEPARATION CYCLE?
- NO → 5
- YES → 4

OPERATE PULL MAGNET PROCEDURE → 1

DISCARD TIPS?
- YES → OPERATE DISCARD TIPS PROCEDURE → GO TO HOME
- NO → GO TO HOME

SEE FIG. 16b

SEE FIG. 17b

SEE FIG. 18b

APPARATUS AND METHOD FOR TRANSFERRING SAMPLES FROM A SOURCE TO A TARGET

FIELD OF THE INVENTION

The present invention relates generally to the field of analytical separation and combining of samples and, more particularly, to a system and apparatus for individually actuating and controlling a multiple array of collection members for transferring samples from a plurality of source vessels to a plurality of target vessels.

BACKGROUND OF THE INVENTION

Analytic and diagnostic procedures in the laboratory often require the transfer of a plurality of samples, simultaneously, from one array of liquid-containing wells to another. In order to transfer, add, collect or combine liquids, various multi-transferring systems have been devised. The most commonly used is a multi-pipette which collects liquid from an array of source wells for transfer to an array of target wells, simultaneously, by application or release of application, respectively, of vacuum force. In operation, the pipette for collecting or releasing of liquid is connected to a single vacuum source provided to all the pipettes in the system so that all samples in the array of wells are collected and released at once.

In recent years, magnetic particles have been used for a variety of separation, purification, and isolation techniques in connection with chemical or biological molecules. In those techniques, a molecule is coupled to a magnetic particle capable of forming a specific binding (hereinafter "affinity binding") with a molecule in a biological sample, which is to be isolated, purified or separated. The biological sample is then brought into contact with the magnetic particle and those biological molecules which bind to the magnetic particles are then isolated by application of a magnetic field.

Various devices have been developed to utilize such magnetic separation techniques in order to transfer the magnetic particles from one location to another. Indeed, magnetic separation technology has passed through several phases in the recent years. The first generation of magnetic separation technology used a two step separation technique involving a separation stand including a magnetic plate placed directly under a micro-plate. These thirty year old simple magnetic plates were composed of permanent magnets encapsulated in plastic which would contact the micro-plate vessels containing the magnetic particle suspensions. The magnetic particles within the suspensions would be drawn to the bottom or the inner surfaces of the wells in the micro-plate and the liquid was drawn out of the well or vessel leaving the magnetic particles behind. In general, such devices are termed "first generation magnetic separators."

One drawback of the "first generation" separators relates to the fact that the stationary permanent magnets positioned below the micro-plates do not come into direct contact with the magnetic particles due to the thickness of the plate and vessel sides. As a result, the magnetic field applied to the individual micro-plate wells is relatively weak due to the distance between the magnetic plate and the magnetic particles and separation is, therefore, somewhat inefficient.

To overcome this drawback, the recent second generation of magnetic separators generally employ a magnetic pipette in a one step separation process, wherein a magnetic rod is inserted into the magnetic solution to capture magnetic particles. Here, magnetic particles are attracted by strong magnetic fields to the rods and then moved out of the magnetic suspension and transferred to another vessel containing fresh washing liquid or reagent solution. The rod is then demagnetized to permit detachment of the magnetic particles into the other liquid.

Such a "second generation magnetic separator" is disclosed, for example, in U.S. Pat. No. 4,292,920. This device includes a single or multi-pin arrangement, corresponding to a micro-well arrangement, which is capable of insertion into the wells of a micro-plate to attract magnetic particles by magnetic force. In one embodiment, the pin is connected to an electromagnet, and by turning the electromagnet on and off the pin becomes magnetized, or non-magnetized, respectively.

Another "second generation magnetic separator" is disclosed in U.S. Pat. No. 5,567,326, which shows an apparatus and method for separating magnetically responsive particles from a nonmagnetic test medium in which they are suspended. The device comprises a plurality of nonmagnetic pins (termed "magnetic field directing elements") arranged in an array, and a magnet positioned normal to the array. Placing the magnet on the array of pins renders all the pins in the array magnetic thereby causing particles to be attracted to them. Removing the magnet causes the pins to become non-magnetic, and consequently the magnetic particles are released from the pins.

The drawbacks of the above "second generation separators" reside in the fact that the magnetic rods or pins come into direct contact with the magnetic particles, so that if rinsing and sterilization is required, the whole apparatus or device has to be washed. Such a procedure is expensive and time consuming. Furthermore, even where the magnetic rods are covered with disposable protective tips, the collection of particles is not efficient since some of the particles remain in the suspension due to surface tension forces. Another drawback of these devices reside in the fact that where a multi-pin device is used to collect magnetic particles from a plurality of wells, all of the pins are fixed to a movable head and travel up and down as a unit such that all of the samples from all the wells have to be collected at once in an "all or none" fashion. Thus, it is not possible to selectively collect particles from only selected wells in an array.

In U.S. Pat. No. 6,409,925, Gombinsky et al. disclose a "third generation magnetic separator." The '925 patent discloses a device wherein each collecting pin can be independently controlled. Specifically, the disclosed magnetic rod design allows for a magnet disposed therein to be freely and independently movable up or down to thereby magnetically energize and de-energize the rod. Thus, each rod is independently magnetized regardless of the magnetization of the other rods. This unique feature permits multiple degrees of freedom (i.e., pin head movement and independent magnet movement) compared to "second generation" systems that have only one degree of freedom.

Accordingly, it would be desirable to improve upon the latest "third generation" magnetic separator technology in various ways to provide a complete control and actuation system that utilizes third generation technology. It would be further desirable to provide such a system with a selectable bottom magnet array and a combinatorial tip loader for the upper pin device.

SUMMARY OF THE INVENTION

The present invention is a control system for transferring a sample from a source vessel to a target vessel. The control system generally includes a vessel unit, a primary transfer unit, an x-drive, a y-drive, a z-drive and a control unit for controlling the drives. The vessel unit includes a translatable support plate for supporting the source vessel and the target vessel thereon and the transfer unit includes at least one transfer device for transferring the sample from the source vessel to the target vessel. The x-, y- and z-drives reciprocally translate one of the support plate and the transfer device in a respective x-direction, y-direction and z-direction, wherein the x, y and z directions define a three axis Cartesian coordinate system.

The present invention may take the form of a control system wherein the primary transfer unit comprises a primary magnet unit and the transfer device uses a magnetic force to attract the sample thereto. Additionally, the vessel drive unit is further preferably in the form of a micro-well drive unit including a translatable support plate for supporting a micro-well tray having at least one of the source vessel and the target vessel thereon.

In a preferred embodiment, the primary magnet unit includes an array of pins and a magnet actuator system for selectively applying and removing the magnetic force at the tip of at least one pin of the pin array. The pin further preferably includes a hollow pin body terminating in a tip and a magnet slidably disposed within the hollow pin body, wherein the magnet actuator system drives the magnet within the hollow pin body to move from a first position adjacent the tip of the pin to a second position away from the tip. When the magnet is adjacent the tip, the magnetic force is applied at the tip and when the magnet is away from the tip, the magnetic force is removed from tip.

The magnet actuator system preferably includes an actuator plate having at least one individually activated electromagnet disposed thereon, an actuator plate drive for reciprocally translating the actuator plate and a magnet rod having a distal end connected to the magnet in the hollow pin body. The magnet rod, which may take the form of a flexible cable, includes a ferromagnetic piston portion engageable with the electromagnet when the electromagnetic is activated for moving the magnet from the first position to the second position upon translation of the actuator plate. Also, the actuator system further preferably includes a piston housing spaced from the actuator plate. The piston housing includes a tension spring connected to the ferromagnetic piston portion of the magnet rod for biasing the piston portion toward the piston housing.

In an alternative embodiment, the magnet actuator system includes a magnet rod having a proximal end and a distal end, and an individually activated magnet rod drive. The distal end of the magnet rod is connected to the magnet in the hollow pin body and the magnet rod drive is connected to the proximal end of the magnet rod for moving the magnet from its first position to its second position.

The magnetic pin control system of the present invention further preferably includes a secondary magnet unit including at least one secondary magnet element supported on a secondary magnet plate, wherein the support plate of the micro-well drive unit is disposed between the pin tip of the primary magnet unit and the secondary magnet element of the secondary magnet unit. The secondary magnet further preferably includes its own y-axis secondary magnet plate drive for reciprocally translating the secondary magnet plate in the y-direction and a z-axis secondary magnet plate drive for reciprocally translating the secondary magnet plate in the z direction.

Like the pin, the secondary magnet element is preferably part of an array of secondary magnet elements which are adapted to be selectively activated and de-activated for alternately applying and removing a magnetic field at a bottom of the micro-well tray. This can be achieved with a secondary magnet actuator system that drives a magnet slidably disposed in a bore of the secondary magnet plate between a first position adjacent the micro-well support plate for applying the magnetic field to a respective well of the micro-well tray, to a second position away from the micro-well support plate for removing the magnetic field from the respective well of the micro-well tray. Here too, the secondary magnet actuator preferably includes an actuator plate having at least one individually activated electromagnet disposed thereon, an actuator plate drive for reciprocally translating the actuator plate and a magnet rod having a distal end connected to the magnet in the secondary magnet plate, wherein the magnet rod includes a ferromagnetic piston portion engageable with the electromagnet when the electromagnetic is activated for moving the magnet from the first position to the second position upon translation of the actuator plate.

The pin control system of the present invention may further include a tip insertion unit for applying a disposable tip to the pin of the primary magnet unit and a tip removal unit for removing the disposable tip from the pin. The tip insertion unit may include a block having a bore formed therein. The bore has a proximal end and a distal end. The proximal end is sized to receive the disposable tip for application to the pin and a pressure source is connected to the distal end of the bore for applying a pressure in the bore for forcing the disposable tip out of the bore. A piston slidably received within the bore may also be provided for forcing the disposable tip out of the bore under the influence of the pressure.

The tip removal unit may include a fork defined by at least one channel having a width corresponding to a diameter of the pin. The channel is adapted to engage the disposable tip of the pin when the pin is brought into the channel.

The present invention further involves a method for transporting a sample from a source vessel to a target vessel. The method generally includes the steps of supporting the source vessel and the target vessel on a translatable support plate, translating the support plate in an x-direction to position the source vessel below a transfer device of a primary transfer unit, translating the primary transfer unit in a y-direction to position the transfer device above the source vessel, translating the primary transfer unit in a z-direction to lower the transfer device into the source vessel, activating the transfer device to collect the sample contained in the source vessel, translating the primary transfer unit in the z-direction to raise the transfer device out of the source vessel, translating the primary transfer unit in the y-direction to position the transfer device above the target vessel, translating the support plate in the x-direction to position the target vessel below the transfer device of the primary transfer unit, translating the primary transfer unit in the z-direction to lower the transfer device into the target vessel and deactivating the transfer device to release the sample from the transfer device into the target vessel. According to the present invention, the x, y and z directions described above define a three axis Cartesian coordinate system.

In a preferred embodiment, the primary transfer unit is in the form of a primary magnet unit and the transfer device is in the form of a pin having a tip. In this case, the activating step involves the step of applying a magnetic force at the tip to attract magnet particles of the sample contained in the source vessel and the deactivating step involves the step of removing the magnetic field from the tip to release the magnet particles from the tip into the target vessel. The magnetic force is preferably applied by moving a magnet within a hollow body of the pin to a first position adjacent the tip of the pin and the magnetic force is removed by moving the magnet to a second position away from the pin tip. Also, the step of moving the magnet to the first position preferably includes the steps of engaging a ferromagnetic piston portion of a magnet rod connected to the magnet with an electromagnet fixed on an actuator plate and translating the actuator plate. Preferably, movement of the piston is biased by a tension spring.

The method of the present invention further preferably includes the step of providing a secondary magnet unit below the translatable support plate opposite the primary transfer unit, wherein the secondary magnet unit includes at least one secondary magnet element supported on a secondary magnet plate. The secondary magnet unit may be translated in the y-direction and the z-direction to position the secondary magnet element under the transfer device of the primary transfer unit.

Additionally, the secondary magnet element may be selectively activated and de-activated for alternately applying and removing a magnetic field at a bottom of the translatable micro-well support plate. The step of selectively activating and de-activating the secondary magnet element preferably includes the step of moving a magnet disposed within a bore of the secondary magnet plate between a first position adjacent the translatable micro-well support plate and a second position away from the translatable micro-well support plate. The magnet may be moved by engaging a ferromagnetic piston portion of a magnet rod connected to the magnet with an electromagnet fixed on an actuator plate and translating the actuator plate.

Moreover, the method of the present invention may further include the steps of translating the primary magnet unit in the y-direction and the z-direction to position the pin tip adjacent a tip insertion unit and applying a disposable tip on the pin with the tip insertion unit. This can be accomplished by applying a pressure within a bore having the disposable tip seated therein, wherein the pressure forces the tip out of the bore and onto the pin.

Furthermore, the method of the present invention may further include the steps of translating the primary magnet unit in the y-direction and the z-direction to position the pin adjacent a tip removal unit and removing a disposable tip from the pin with the tip removal unit. This can be accomplished by positioning the pin within a channel of a fork of the tip removal unit and lifting the pin, wherein the disposable tip engages the fork and is removed from the pin.

Of course, the system can also be operated by selecting any pin combination within the array permitting quantitative collection of particles from a given magnetic suspension. This feature of quantitative separation and transfer allows for dividing a sample into sub-samples. Also, the present invention allows for the sample particles to be washed efficiently with a "flip-flop" movement of particles due to magnets moving under the sample wells.

The present invention further involves a system for transferring samples from a source vessel to a target vessel including a transfer device having a hollow body and an actuating element movably disposed in the hollow body between a first and a second position. Movement of the actuating element causes a sample in proximity to the transfer device to be alternately collected and released from the transfer device. The system further includes an actuator plate having at least one individually activated electromagnet disposed thereon, an actuator plate drive for reciprocally translating the actuator plate and an actuator rod having a distal end connected to the actuating element in the hollow body of the transfer device. The actuator rod includes a ferromagnetic piston portion engageable with the electromagnet when the electromagnet is activated for moving the actuating element from the first position to the second position upon translation of the actuator plate.

The preferred embodiments of the control system as well as other objects, features and advantages of this invention, will be apparent from the following detailed description, which is to be read in conjunction with the accompanying drawings.

BRIEF DESCRIPTION OF THE DRAWINGS

FIGS. 12a and 12b is a flow chart showing operation of the system according to the present invention.

DETAILED DESCRIPTION OF THE PREFERRED EMBODIMENTS

Figure 1:
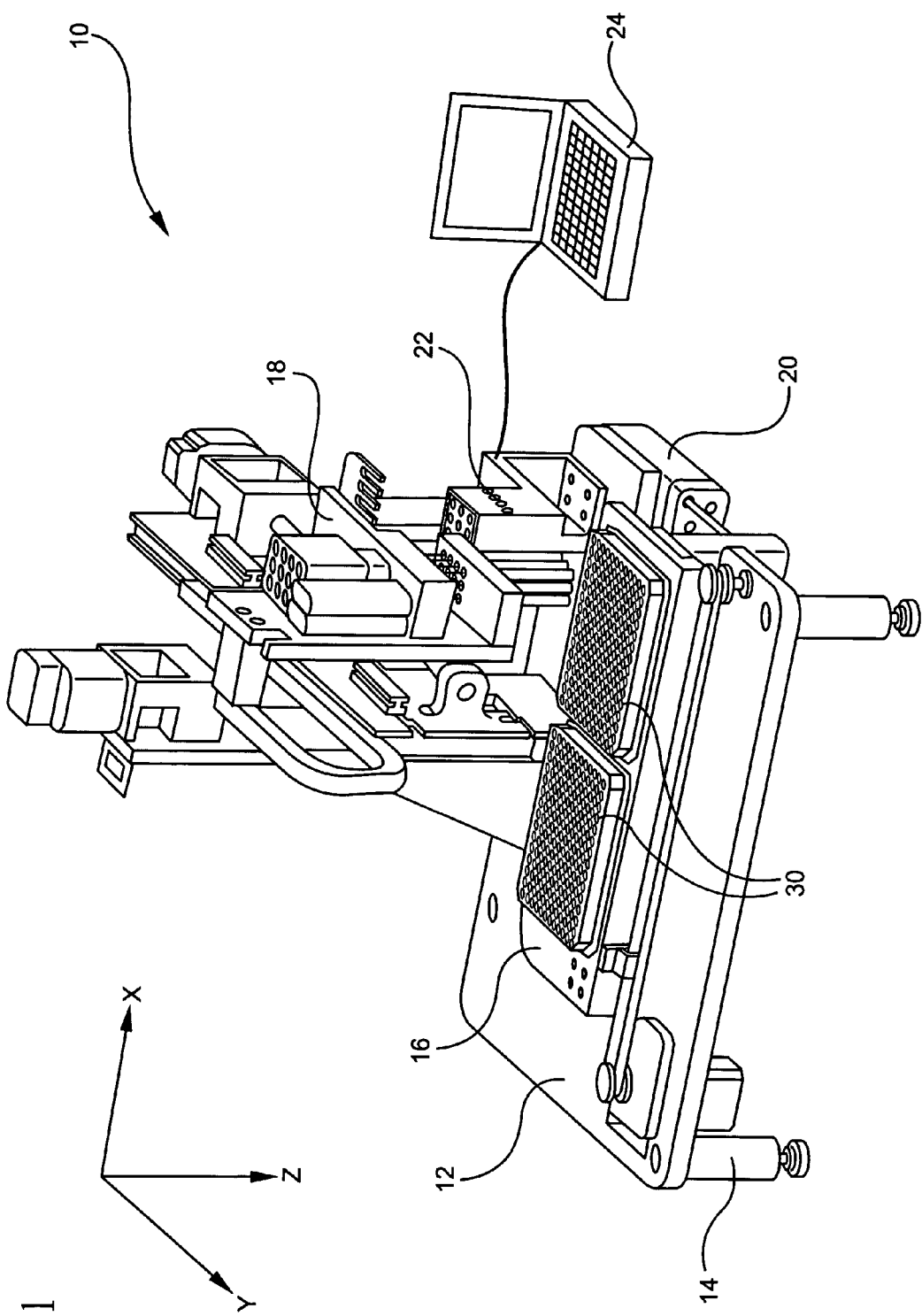
FIG. 1 is a top perspective view of the overall system formed in accordance with the present invention.

Referring first to FIG. 1, the pin control system 10 of the present invention generally includes five major functional components provided on a supporting structure or frame 12 having a plurality of legs 14 for supporting the system 10 on a surface. The major functional components of the system 10 include a vessel unit 16, a primary transfer unit 18, a secondary magnet unit 20, a tip insertion/removal station 22 and a central control unit 24.

Figure 2:
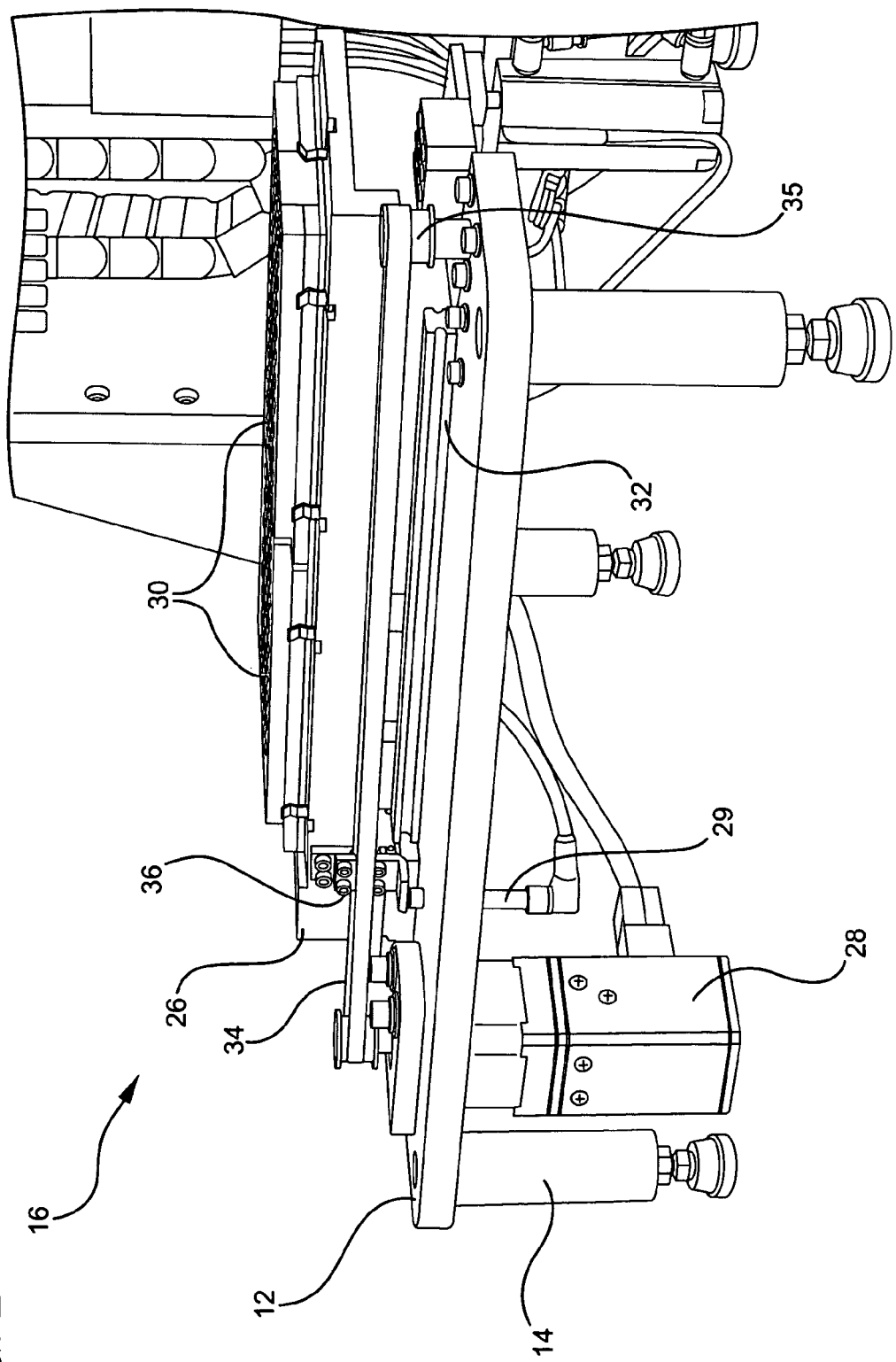
FIG. 2 is a top perspective view of the system shown in FIG. 1 with the micro-well tray drive unit shown in greater detail.

Referring additionally to FIG. 2, the vessel unit 16 preferably includes a translatable support plate 26 and a motor 28 for reciprocally translating the support plate in the x-direction with respect to the system frame 12, as shown in FIG. 1. The translatable support plate 26 supports a source vessel containing a sample to be transferred and a target vessel to which the sample is transported. It is of course conceivable for the support plate 26 to support multiple samples which can be simultaneously transported from respective source vessels to respective target vessels. In a preferred embodiment, the source and target vessels are defined in one or more micro-well trays 30 and the translatable support plate 26 is adapted to support at least one and preferably two standard size micro-well trays having a matrix of n wells. In a preferred embodiment, the matrix of wells carries a magnetic suspension for bio-analytical processes and synthesis therein. It is also conceivable that additional micro-well support plates 26 can be provided on the system frame 12 depending on the system requirements. The support plate 26 further preferably has an open frame construction so that the bottoms of the micro-well trays are accessible from below by the secondary magnet unit 20, as will be described in further detail below.

The support plate 26 is engageable with a rail 32 fixed to the system frame 12 to facilitate smooth translation back and forth in the x-direction. The micro-well motor 28 may be coupled to the plate 26 via a belt 34 and pulley 35 arrangement, whereby the plate includes a carriage 36. The micro-well motor 28 is preferably a standard compact stepper motor. A suitable stepper motor for the present invention is Festo Product No. MTRE-ST, which is a two phase hybrid stepper motor with an integrated power amplifier.

Figure 3:
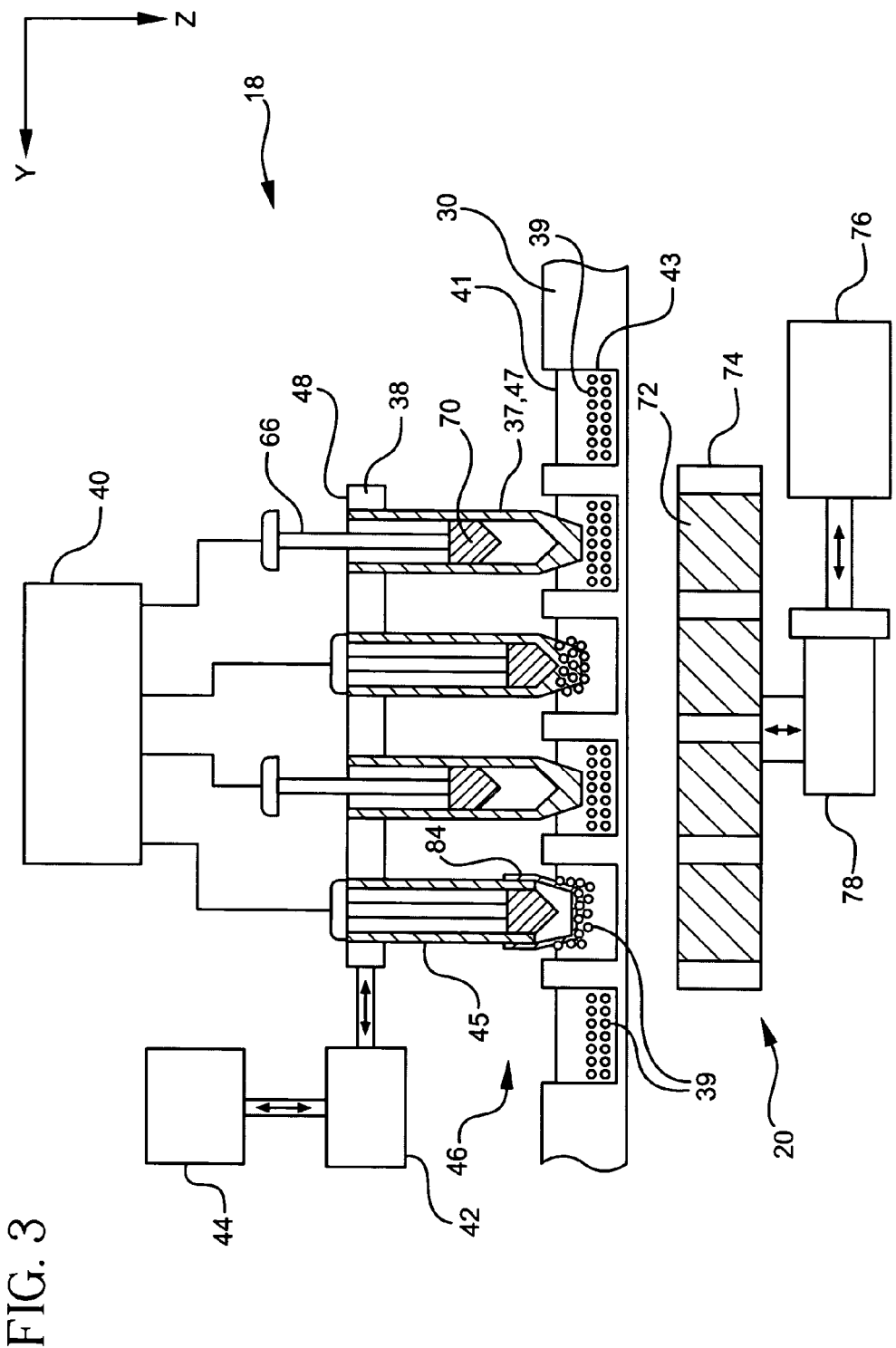
FIG. 3 is a schematic diagram of the functional components of the primary magnet unit and the secondary magnet unit.

FIG. 3 is a schematic diagram showing the functional components of the primary transfer unit 18 and the secondary magnet unit 20. The primary transfer unit 18 generally includes at least one transfer device 37 for transporting a sample from the source vessel to the target vessel. Preferably, and as will be discussed in further detail below, the primary transfer unit 18 includes a head assembly 38 supporting an array of transfer devices 37, wherein each transfer device is capable of being selectively activated to transfer samples from respective source vessels to respective target vessels.

Figure 9:
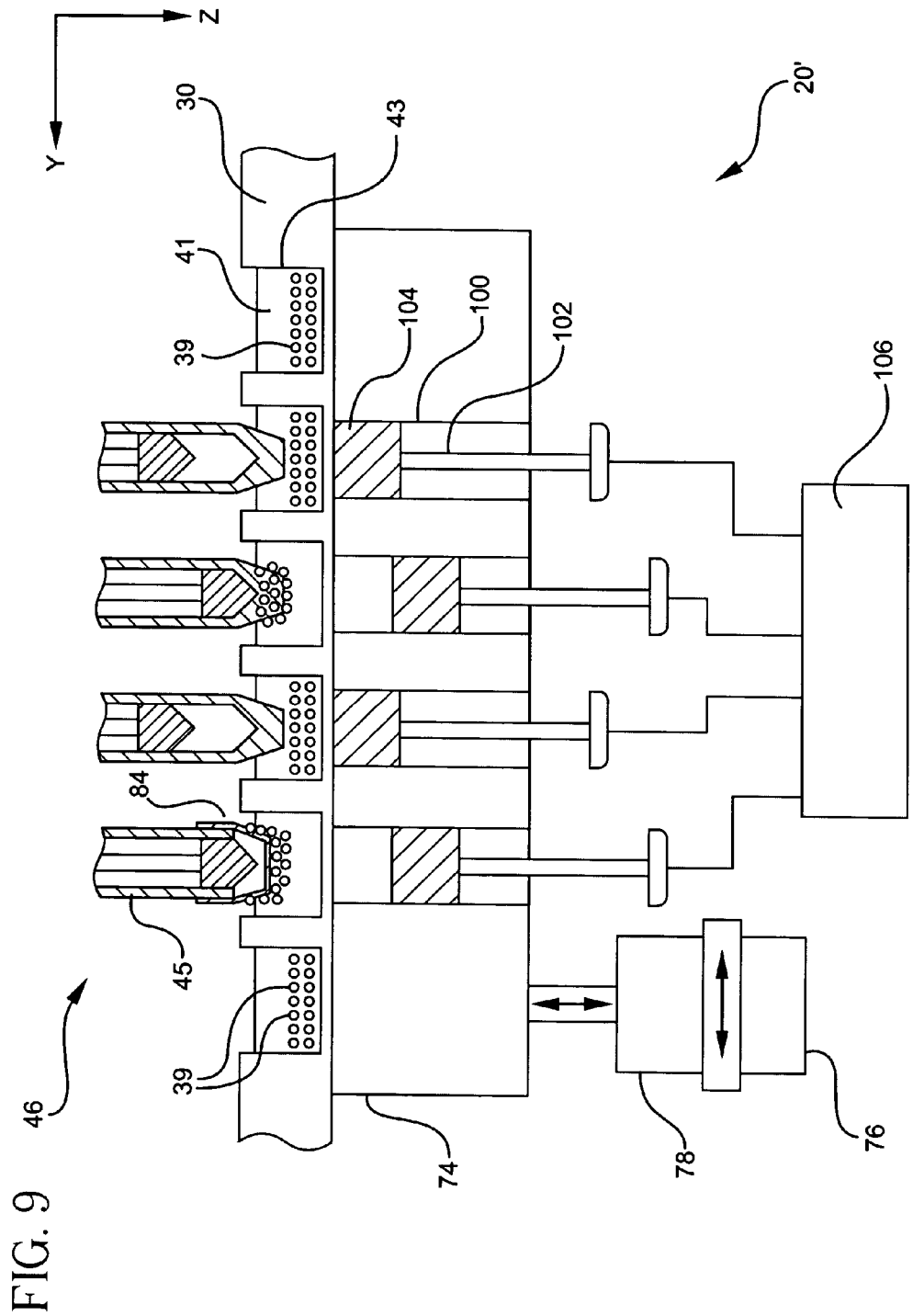
FIG. 9 is a general schematic diagram of the functional components of the preferred embodiment of the secondary magnet unit.
Figure 10:
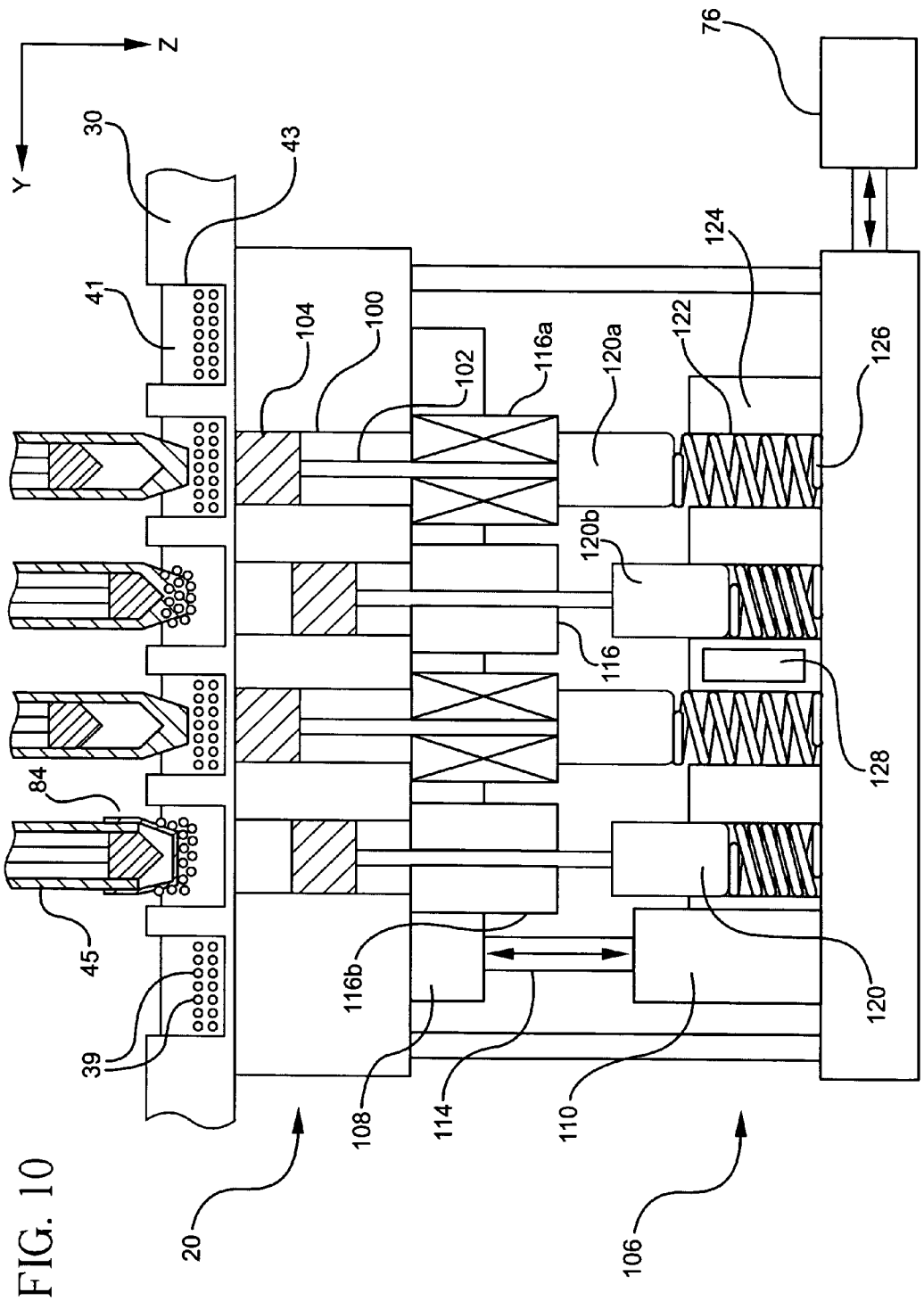
FIG. 10 is a cross-sectional view of the preferred embodiment of the secondary magnet rod actuator system of the secondary magnet unit.

In a preferred embodiment, the primary transfer unit 18 is in the form of a primary magnet unit and the transfer device 37 is in the form of an array 46 of pins 47, each having a hollow pin body 45 terminating in a tip 49. As shown in FIGS. 3, 9 and 10, the tips 49 may be integral with the hollow pin body, or, as will be discussed in further detail below, in the preferred embodiment, the tips take the form of disposable tips 84, which are separable from the body of the pins.

The primary magnet unit 18 further includes an actuator system 40, a y-axis motor 42 and a z-axis motor 44. As will be explained in further detail below, the multi-pin head assembly 38 is driven in the y and z directions by the respective motor 42 and 44 to interact with the micro-well trays 30 driven in the x-direction by the micro-well drive unit 16. Thus, a three-axis Cartesian coordinate, system is established.

It is to be understood that the arrangement of the x-drive 28, y-drive 42 and z-drive 44 is described herein in an exemplary preferred embodiment. Those skilled in the art will appreciate that the three axis drives may be positioned in different arrangements, wherein, for example, the y-drive and/or the z-drive translate the support plate 26 in the y-direction and/or the z-direction. Similarly, the support plate 26 supporting the micro-well trays 30 may be stationary, whereas the transfer device 37 may be provided with three-axis movement. Such alternate drive arrangements are intended to come within the scope of the invention.

Figure 4:
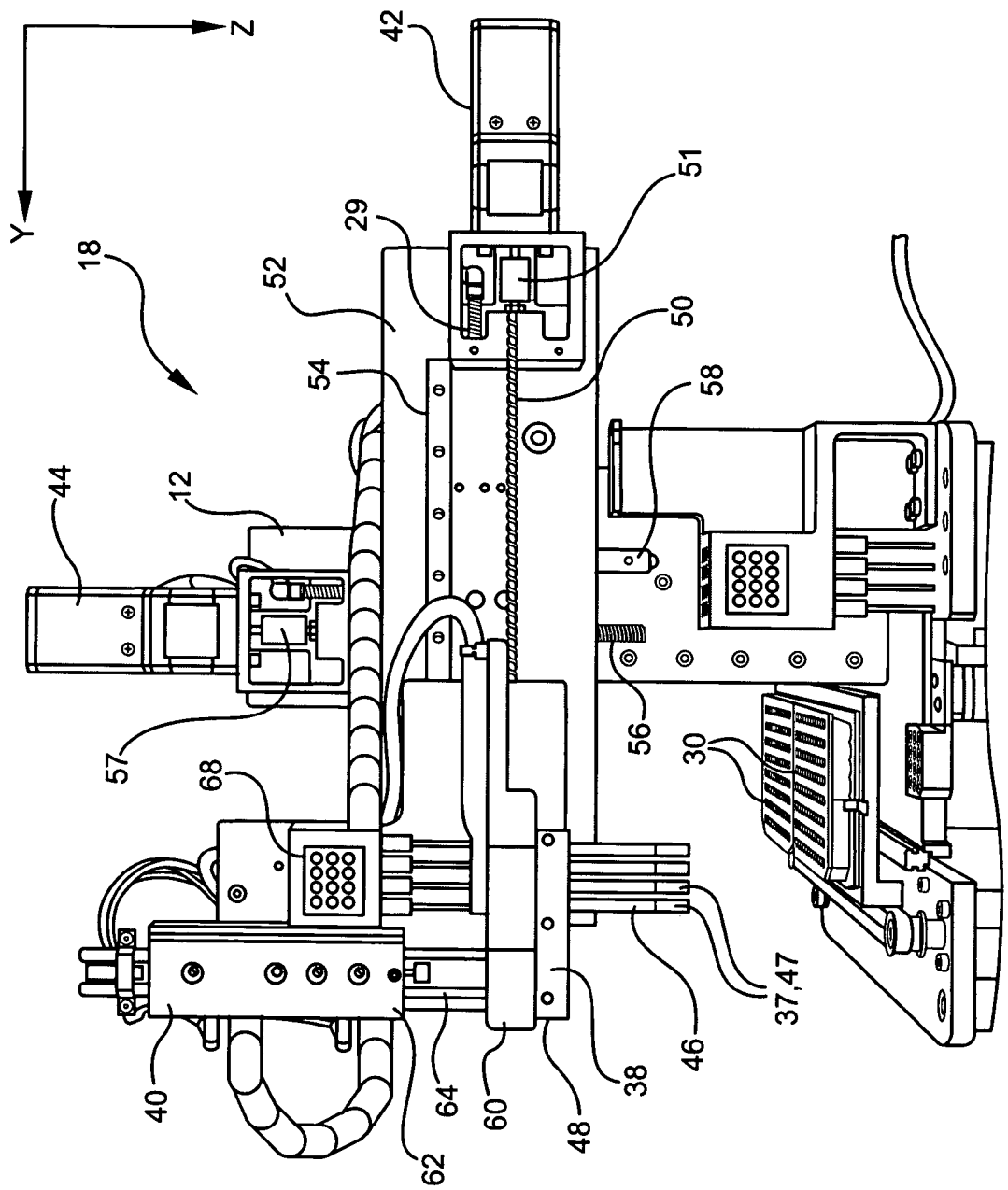
FIG. 4 is a plan view of the system shown in FIG. 1 with the primary magnet unit shown in greater detail.

Returning to the preferred embodiment shown in FIG. 4, the transfer devices 37 or pins 47 are secured to a bottom leg of an angle plate 48 in a conventional manner so that the pins 37, 47 point downward in the z-direction. The array 46 shown in the drawings is a 4×3 array of twelve devices/pins 37, 47, but other numbers or arrays of pins may be utilized. The upwardly extending leg of the angle plate 48 is coupled to the y-axis motor 42 via a ball screw 50 and actuator 51. In this manner, the angle plate 48 with the pin array 46 are translatable in the y-direction by the y-axis motor 42. The angle plate 48 and the y-axis motor 42 are in turn attached to a z-axis plate 52, which is translatable in the z-direction. The angle plate 48 is preferably supported on a rail 54 fixed to the z-axis plate 52 to permit translation of the angle plate, and thus the pin array 46, in the y-direction. Linear bearings (not shown) may be provided on the angle plate 48 to facilitate smooth translation.

The z-axis plate 52 is coupled to the z-axis motor 44 by a similar ball screw 56, actuator 57 and rail 58 arrangement. In particular, the z-axis plate 52 is preferably, translatably supported on a rail 58 fixed to the system frame 12 so that the z-axis plate, along with the pin array 46, can be driven in the z-direction by the z-axis motor with respect to the system frame.

Figure 5:
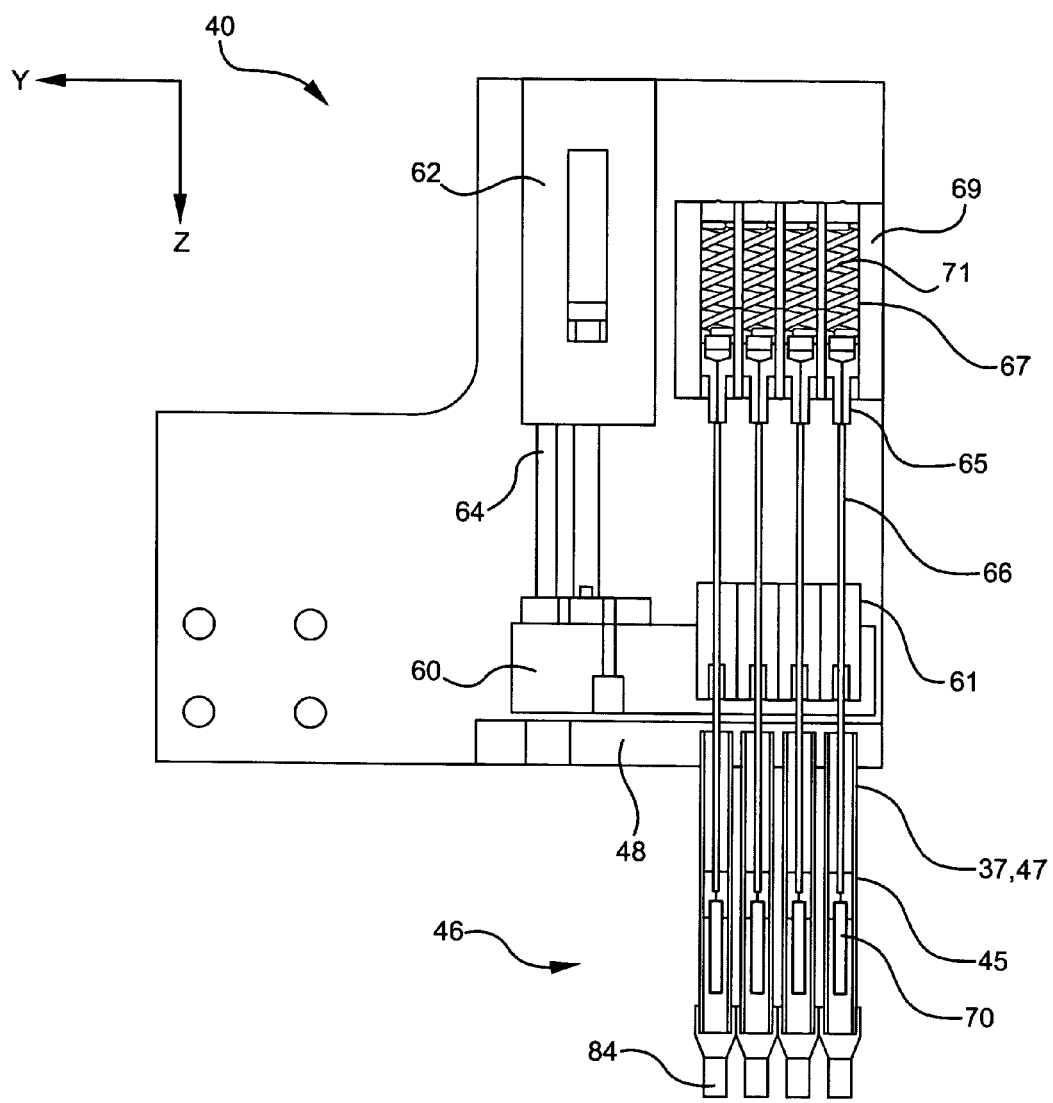
FIG. 5 is a cross-sectional view of the preferred embodiment of the magnet rod actuator system of the primary magnet unit.

Referring additionally to FIG. 5, the transfer device 37 is preferably in the form of a pin 47 having a hollow body 45 and a removable tip 84 attached at an end thereof. The pin 47 further includes an actuating element 70 movably disposed in the body 45 between a first position adjacent the tip 84 and a second position away from the tip. This movement of the actuating element 70 causes a sample in proximity to the tip 84 of the transfer device 37 to be alternately collected and released from the tip of the transfer device.

In a preferred embodiment, the actuating element 70 is a magnet which applies a magnetic force at the tip 49, 84 of the pin 47 when it is positioned adjacent the tip to attract magnetic particles 39 suspended in the liquids 41 contained in the wells 43 of the micro-well tray 30, as shown in FIG. 3. When the magnet 70 is retracted or withdrawn away from the tip 49, 84 of the pin 47, the magnetic force is thereby removed and the magnetic particles 39 are released from the tip. This interaction between the magnet rods 66 and the pins 47 and the resulting magnetic operation of the pin array 46 is further described in U.S. Pat. No. 6,409,925 to Gombinsky et al., the disclosure of which is incorporated herein by reference.

In an alternative embodiment, the actuating element may take the form of a piston or a plunger which alternately creates a positive pressure or a suction within the hollow body 45. Such positive pressure may be used to discharge a sample 41 from an opening at the tip of the transfer device. Conversely, such suction may be used to draw in a sample through an opening of the tip. This operation is similar to that of a conventional syringe, pipette, or other known device for supplying and/or releasing a vacuum.

In either embodiment, individual movement of the actuating elements 70 with respect to the pins 37, 47 is controlled by the actuator 40. Such "combinatorial" movement can be achieved pneumatically, wherein each pin 37, 47 is connected to air lines for the supplying and release of pneumatic forces to move the actuating elements 70 as desired. Alternatively, solenoid valve-equipped pipettes, instead of magnets can also be used with the present invention for the transportation of beads. However, in a preferred embodiment, movement of the actuating elements 70 is achieved through an electronically controlled clutch-type mechanism, as will be described in further detail below.

In the preferred embodiment, the transfer device actuator system 40 includes an actuator plate 60 fixed to a linear drive 62, such as a pneumatic actuator, via one or more piston rods 64 or other form of connection for reciprocally translating the actuator plate in the z-direction. The linear drive 62 is preferably a pneumatic cylinder connected to inlet and outlet air lines and in electrical communication with the central control unit 24. The actuator plate 60 includes a plurality of individually activated electromagnets 61 fixed thereon. The number and arrangement of the electromagnets 61 preferably matches the number and arrangement of pins 37, 47 in the multi-pin array 46. The electromagnets 61 each include an interior bore to translatably receive an actuator rod 66 having the actuating element 70 attached at an end thereof.

Figure 6:
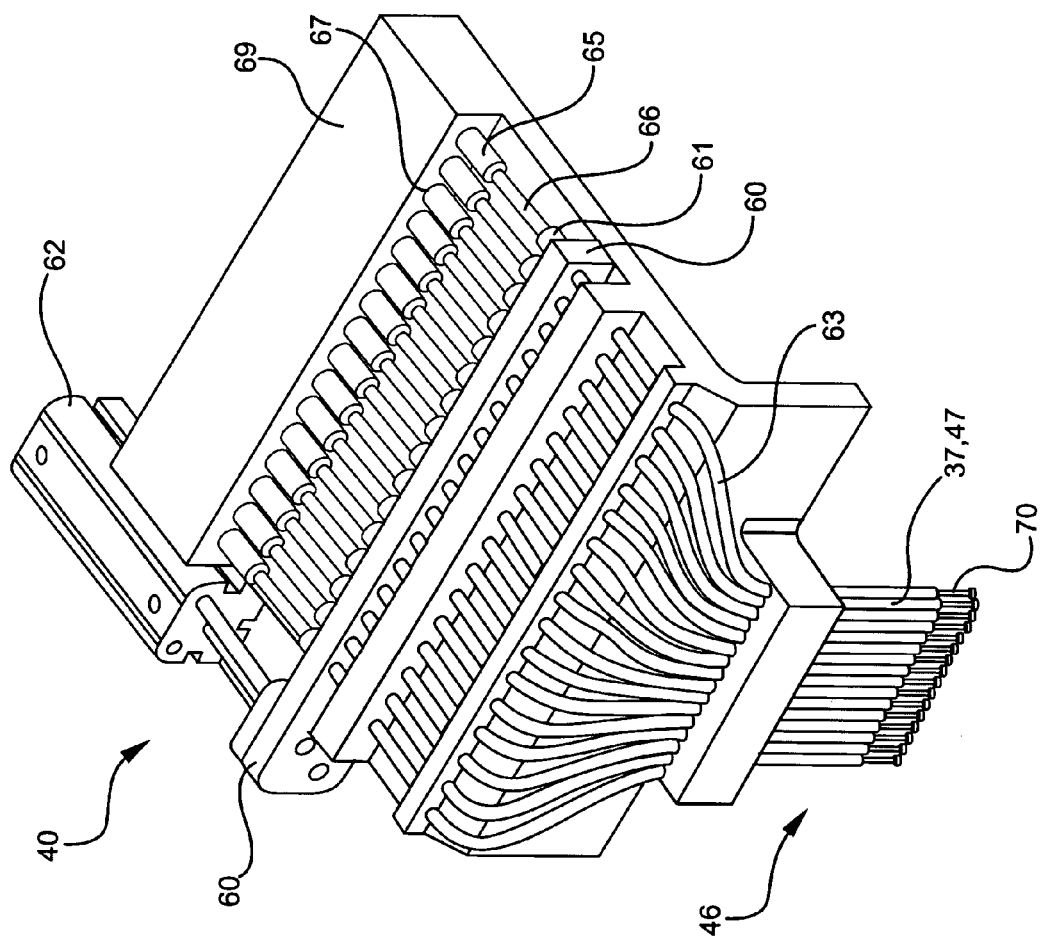
FIG. 6 is a top perspective view of an alternative embodiment of the magnet rod actuator system of the primary magnet unit.

The actuator rod 66 may be a semi-rigid tubular member oriented vertically with respect to the pins 37, 47, as shown in FIG. 5, or the rod may take the form of a flexible cable enclosed in a flexible cable guide 63, allowing for more condensed and angular orientations of the actuator system 40, as shown in FIG. 6. In both embodiments, at their ends opposite the actuating element 70, the actuator rods 66 are each fixed to a ferromagnetic piston 65 slidably received in a respective bore 67 of a piston housing 69. Also disposed in each bore 67 of the piston housing 69 is a tension spring 71 connected between the housing and the ferromagnetic piston 65 to maintain the actuator rod 66 in an upward retracted position.

In operation, the individual transfer devices 37 to be activated are preferably selected with the control unit 24. Alternatively, selection may be made via a control pad 68 disposed on the piston housing 69. The control pad 68 may be fixed to the piston housing 69, as shown in FIG. 4, or it may be provided on the frame 12 or other convenient location. The respective electromagnets 61 for the selected devices/pins 37, 47 may be electrically activated, whereby an attractive magnetic force is imposed on the selected electromagnets. Specifically, the linear drive 62 is activated to bring the actuator plate 60, along with the energized electromagnets 61, toward the ferromagnetic pistons 65 disposed in the piston housing 69. As the actuator plate 60 nears the piston housing 69, the energized electromagnets 61 attract their respective ferromagnetic pistons 65 drawing the pistons into contact with the electromagnets against the tension force of the spring 71.

The linear drive 62 is then reversed wherein the actuator plate 60 is driven away from the piston housing 69 in the z-direction. As the actuator plate 60 moves away from the piston housing 69, only those ferromagnetic pistons 65 that have been magnetically drawn into contact with a respective electromagnet 61 are moved together with the actuator plate. In this regard, the magnetic force applied by the electromagnets 61 is greater than the tension force applied by the tension springs 71 so that the selected ferromagnetic pistons 65 will move together with the actuator plate 60. This movement, in turn, moves the actuating element 70 disposed at the opposite end of the actuator rod 66 toward the tip of its respective pin, thereby applying a magnetic force at the tip.

The remaining non-selected pistons 65 maintain their original positions within with the piston housing 69 by virtue of the tension force applied by the tension springs 71. Thus, the actuating elements 70 in the respective pins 47 of the non-selected pistons 65 will not move toward the pin tip, thereby leaving these tips without a magnetic force.

Figure 7:
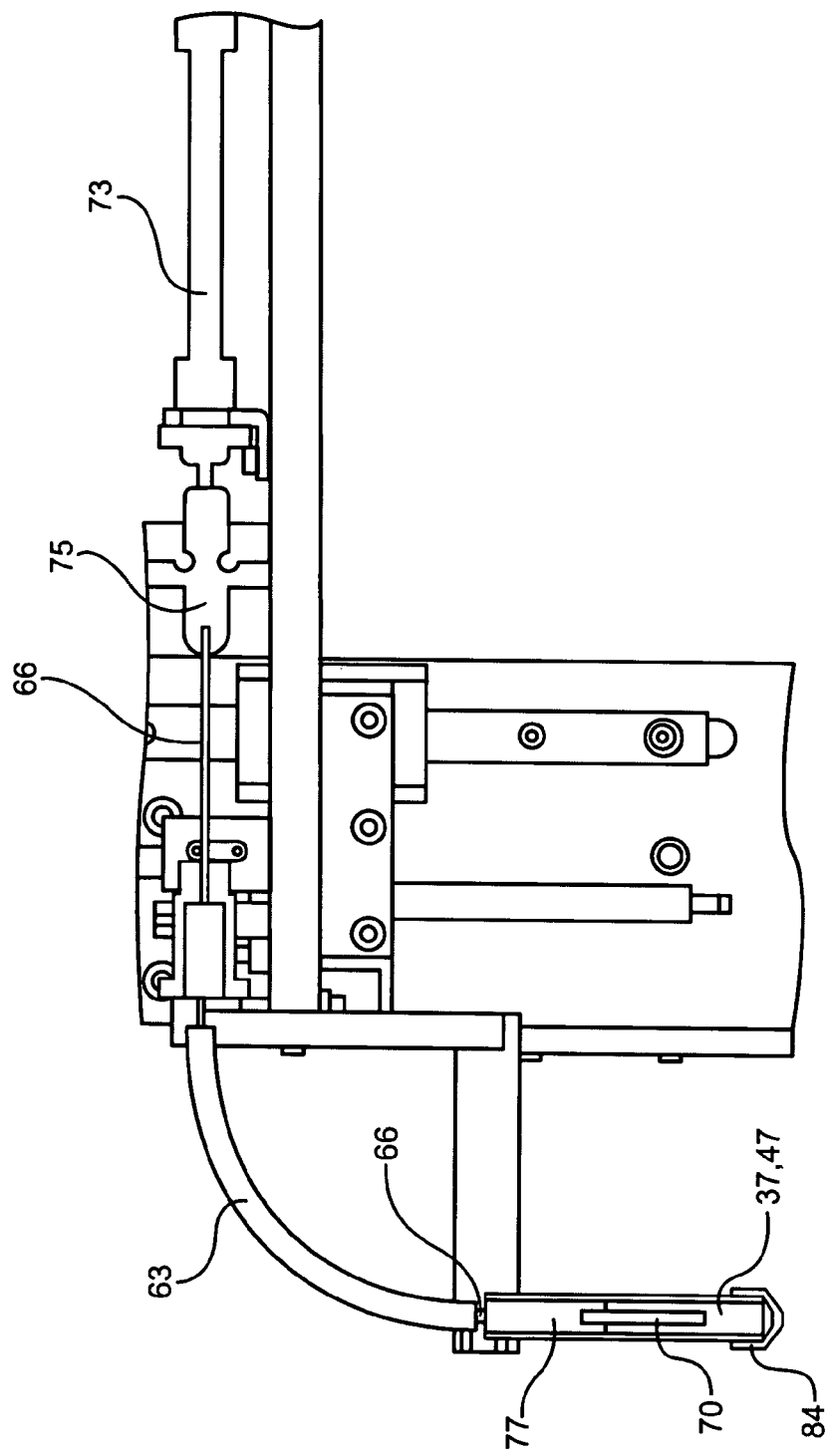
FIG. 7 is a cross-sectional view of still another alternative embodiment of the magnet rod actuator system of the primary magnet unit.

FIG. 7 shows yet another alternative embodiment for achieving this "combinatorial" technique. In this embodiment, rather than using an electromagnet clutch-type mechanism, as described above, each actuator rod 66 is coupled to its own individually activated rod drive 73 via a piston 75. The remaining components are the same in that a cylindrical actuating element 70, such as a magnet, is slidingly disposed in a respective pin 47 and the magnet is connected to an actuator rod 66, which in this case is preferably a flexible cable encased within a flexible cable guide 63. A magnet or iron piston 77 may be provided between the magnet 70 and the flexible rod 66 to improve stability. The rod drive 73 may be a pneumatic linear drive-type cylinder, as described above, and is preferably controlled by the system controller 24 to selectively drive the rod 66 to move the magnet 70 toward and away from the pin tip 84 to alternately apply and remove the magnetic force.

The present invention contemplates the use of any one of the combinatorial techniques described herein for the primary magnet unit 18 and, as will be discussed in further detail below, for the secondary magnet unit 20. Also, as mentioned above, the system of the present invention would also work to individually control the primary magnet combinatorial technique described in U.S. Pat. No. 6,409,925 to Gombinsky et al.

Figure 8:
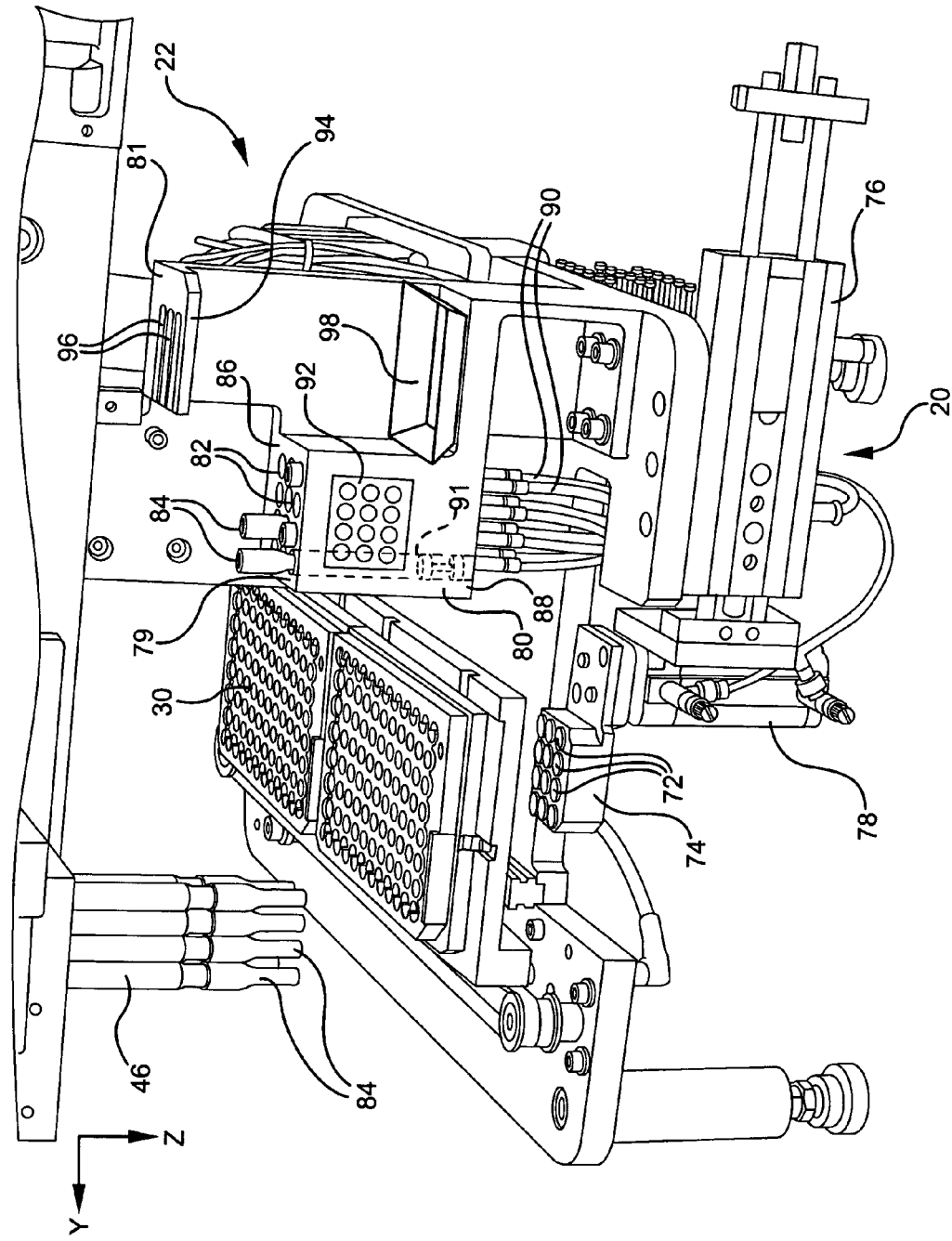
FIG. 8 is a top perspective view of the system shown in FIG. 1, with the secondary magnet unit, the tip insertion/removal station shown in greater detail.

Returning now to FIG. 3, and referring additionally to FIG. 8, in one embodiment, the secondary magnet unit 20 includes an array of secondary magnet elements, such as permanent magnets 72 fixed on a movable secondary magnet plate 74. The spacing and arrangement of the permanent magnets 72 generally coincides with the spacing and arrangement of the array 46 of pins 47 of the primary magnet unit 18. Thus, in the drawings, a 4×3 array of twelve permanent magnets 72, matching the spacing and arrangement of the pins 47, is provided in the secondary magnet plate 74. A y-axis magnet plate drive 76 and a z-axis magnet plate drive 78 are connected to the secondary magnet plate 74 to respectively, reciprocally translate the magnet plate in the y and z-directions. The magnet plate drives 76 and 78 are preferably pneumatic cylinders connected to inlet and outlet air lines and in electrical communication with the central control unit 24.

In operation, the magnet plate 74 is controlled to move in a complementary manner with the movement of the pin array 46 of the primary magnet unit 18. Briefly, the magnet plate 74 is fixed in the x-direction in aligned orientation with the magnet pin array 46 and will generally translate together with the pin array in the y-direction so that each well of the micro-tray 30 having a pin positioned thereover will also have a permanent magnet 72 positioned therebelow. Moreover, as will be described in further detail below, the magnet plate 74 is also controlled to complement the movement of the magnet rods 66 in the z-direction within the pin array 46 to facilitate removal or "washing" of the magnetic particles from the pin tips. This "washing" technique is also described in U.S. Pat. No. 6,409,925 to Gombinsky et al., the disclosure of which is incorporated herein by reference.

Alternatively, the secondary magnet plate 74 can be fixed in the z-direction and the permanent magnets 72 can be replaced with electromagnets which are selectively activated and de-activated for the alternate application of a magnetic field on the magnetic particles in the wells of the micro-plate 30.

As mentioned above, in the preferred embodiment, the secondary magnet unit can be designed similar to the primary magnet unit 18, wherein individual secondary magnet rods can be selected in a manner similar to the primary magnet unit. Referring now to FIG. 9, which is a schematic diagram showing the functional components of the preferred embodiment of a secondary magnet unit 20', the secondary magnet plate 74 in this case includes an array of cylindrical bores 100 supporting a corresponding array of slidable secondary magnet rods 102, each having a magnet 104 fixed to a distal end thereof. Like the array of permanent magnets 72 described above, the array of slidable magnet rods 102 preferably matches, in number and arrangement, the array of pins 47 of the multi-pin array 46.

With the magnet plate 74 positioned below the micro-well tray 30 by the y- and z-drives 76 and 78, as described above, the magnet rods 102 are selectively controlled by a secondary magnet actuator 106. When a magnet rod 102 is fully inserted into its respective bore 100, a magnetic field is applied to attract the magnetic particles 39 suspended in the liquids 41 contained in the wells 43 of the micro-well tray 30 adjacent the inserted magnet rod. When the magnet rod 102 is retracted or withdrawn, the magnet 104 moves away from the bottom of the micro-well tray 30, thereby releasing the magnetic particles 39 free at the bottom of the well 43, ready to be picked up (or not) by a specifically chosen pin tip 49.

As mentioned above, individual movement of the magnet rods 102 with respect to the secondary magnet plate 74 is controlled by the secondary magnet actuator 106. Again, such movement can be achieved pneumatically, wherein each cylindrical bore 100 in the magnet plate 74 is connected to air lines for the supplying and release of pneumatic forces to move the magnet rods 102 as desired. However, in a preferred embodiment, the secondary-magnet unit 20' utilizes an electromagnetic clutch-type mechanism, as described above with respect to the primary magnet unit 18 and as shown in FIG. 10.

Specifically, as shown in FIG. 10, the secondary magnet actuator 106 generally includes an actuator plate 108 fixed to a linear drive 110, such as a pneumatic actuator, via one or more piston rods 114 or other form of connection for reciprocally translating the actuator plate in the z-direction. The linear drive 110 is preferably a pneumatic cylinder connected to inlet and outlet air lines and in electrical communication with the central control unit 24. The actuator plate 108 includes a plurality of individually activated electromagnets 116 fixed thereon. The number and arrangement of the electromagnets 116 matches the number and arrangement of secondary magnets 104 of the secondary magnet unit 20'. The electromagnets 116 each include an interior bore 118 to translatably receive a respective secondary magnet rod 102 having a secondary magnet 104 attached at an end thereof.

The magnet rod 102 may be a semi-rigid tubular member oriented vertically with respect to the pins 47, as shown in FIG. 10, or the rod may take the form of a flexible cable enclosed in a flexible cable guide allowing for more condensed and angular orientations of the actuator system. In any event, at their ends opposite the magnet 104, the magnet rods 102 are each fixed to a ferromagnetic piston 120 slidably received in a respective bore 122 of a piston housing 124. Also disposed in each bore 122 of the piston housing 124 is a tension spring 126 connected between the housing and the ferromagnetic piston 120 to maintain the magnet rod 102 in a downward retracted position.

In operation, application of a magnetic force to individual wells 43 of the micro-well plate 30 may be selected via a control pad 128 disposed on the piston housing 124. The respective electromagnets 116a for the selected secondary magnets 104 are then electrically activated, whereby an attractive magnetic force is imposed on the selected electromagnets. The linear drive 110 is then activated to bring the actuator plate 108, along with the energized electromagnets 116, toward the ferromagnetic pistons 120 disposed in the piston housing 124. As the actuator plate 108 nears the piston housing 124, the energized electromagnets 116a attract their respective ferromagnetic pistons 120a drawing the pistons into contact with the electromagnets against the tension force of the spring 126.

The linear drive 110 is then reversed wherein the actuator plate 108 is driven away from the piston housing 124 in the z-direction. As the actuator plate 108 moves away from the piston housing 124, only those ferromagnetic pistons 120a that have been magnetically drawn into contact with a respective electromagnet 116a are moved together with the actuator plate. In this regard, the magnetic force applied by the electromagnets 116a is greater than the tension force applied by the tension springs 126 so that the selected ferromagnetic pistons 120a will move together with the actuator plate 108. This movement, in turn, moves the secondary magnet 104 disposed at the opposite end of the magnet rod 102 toward the micro-well plate 30, thereby applying a magnetic force at the adjacent well 43.

The remaining non-selected pistons 120b maintain their original positions within the piston housing 124 by virtue of the tension force applied by the tension springs 126. Thus, the magnets 104 of the non-selected pistons 120b will not move toward the micro-well tray 30, thereby leaving these adjacent wells 43 without a magnetic force.

In all of the above embodiments, movement in the z-direction of the secondary magnets 72 or 104 below the micro-well plates 30, in conjunction with movement in the z-direction of the multi-pin head 46 has the desired effect of removing or "washing" the magnetic particles 39 from the pin tips. This so called "washing" involves the dipping and raising of the pins 47 into and out of the wells 43 of the micro-plate 30 both with and without the magnetic rods 66 inserted into the pins. The secondary magnets 72 or 104 can also be selected with regard to size and strength so that the described up and down motion will create a concentrated "button" of separated magnetic particles 39 to gather at the bottom of the selected wells 43.

Returning to FIG. 8, the tip insertion/removal station 22 will now be described. In general, the tip insertion/removal station includes a tip insertion unit 79 for applying the disposable tips 84 to the ends of the pins 47 of the multi-pin array 46 and a tip removal unit 81 for removing the tips from the pins after use.

The tip insertion unit 79 generally includes a manifold block 80 fixed to the system frame 12 and having an array of cylindrical bores 82 formed therethrough. The spacing and arrangement of the bores 82 coincides with the spacing and arrangement of the pins 47 within the pin array 46 of the primary magnet unit 18. Thus, in the drawings a 4×3 array of twelve cylindrical bores 82, matching the spacing and arrangement of the pins 47, is provided in the manifold block. The cylindrical bores 82 are also sized to respectively receive a disposable protective tip 84 which is insertable and removable from a respective pin 47 of the primary magnet unit 18. The tips 84 are loaded into the cylindrical bores 82 at the top face 86 of the manifold block 80 so that their tapered ends point downward.

The manifold block 80 may be loaded manually with a plurality of pin tips 84 or the tip loading may be automated either by feeding single pin tips into the cylindrical bores 82 or by exchanging a complete manifold block with pin tips pre-loaded. For example, the pin tips 84 may be marshaled from a batch, wherein single oriented tips are fed to respective cylindrical bores 84 in the block 80, by a conventional vibratory feeder connected to the manifold block. Alternatively, the entire manifold block 80 with spent tips 84 can be exchanged with a new block by a small robot. In this manner, the block 80 can be pre-loaded away from the system and kept sterile until just prior to use. This method further eliminates down time of the system for loading tips. In either case, the system is thus provided with a higher efficiency.

Connected to each cylindrical bore 82 at the bottom face 88 of the manifold block 80 is an air supply line 90 connected at its opposite end to an air supply source (not shown) for supplying at least a positive air pressure to the cylindrical bore. Furthermore, a tip loading piston 91 is slidably disposed within each cylindrical bore 82 to force the tips 84 onto their respective pins 47 during tip insertion. Preferably, selection of the tips to be loaded is made via the central control unit 24. Alternatively, a tip selection control pad 92 can be provided on the manifold block 80 to select which tip loading pistons 91 within the cylindrical bores 82 are to be activated with air pressure. The air stream is preferably guided through a special tube to prevent contamination of tips and plates.

The air supply line 90 and air supply source may be configured to also provide a negative pressure or vacuum to the cylindrical bore 82 to aid in tip removal from the pins 47. In such a case, the bore 82 must be cleaned and disinfected prior to reloading with clean tips.

Alternatively, the tip insertion/removal unit 22 may further include a tip removal fork 94 attached to the manifold block 80 or to the system frame. The tip removal fork 94 includes a plurality of open channels 96 facing in the y-direction toward the pin array 46 of the primary magnet unit 18. The number of channels 96 provided in the fork 94 corresponds to the number of rows of pins 47 oriented in the y-direction of the pin head 46. The width of the channels 96 is slightly larger than the diameter of the pins 47, but slightly smaller than the upper rim of the disposable plastic tips 84 inserted on the pins.

In operation, the manifold block 80 is first manually or automatically loaded with a plurality of pin tips 84. Alternatively, a new pre-loaded block 80 can be installed on the system frame 12. The pin array 46 of the primary magnet unit 18 is positioned above the manifold block by the y and z stepper motors 42 and 44 and then gently brought down in the z-direction until the ends of the pins 47 are in close proximity to the disposable tips 84. The desired tips 84 can then be entered in the control unit 24, whereby a burst of air pressure supplied by the respective air lines 90 will drive the selected tip loading pistons 91 upwardly to frictionally engage the tips 84 onto the pins 47. To release the air, so that the tips will not become contaminated, a special tube is connected to the bore 82 beneath piston 91 when at its upper position.

For removal of tips 84 from the pins 47, a negative pressure or vacuum can be provided through the air line 90 for pulling the tips off the pins when the pin array 46 is positioned over the manifold block 80. However, in the preferred embodiment, a separate tip removal unit 81 is provided. The tip removal unit 81 includes a tip removal fork 94 having a plurality of channels 96 generally matching in width to the diameter of the pins 47 of the pin array 46. The pin array 46 is brought into engagement with the tip removal fork 94, whereby individual rows of pins 47 are received within the channels 96 of the fork and such that the tips 84 are positioned below the fork. The pin array 46 is then elevated in the z-direction, whereby the fork 94 will contact the upper rim of the tips 84 preventing the tips from moving further along with their respective pins 47. A tip receptacle 98 can be provided below the tip removal fork 94 to catch the tips 84 removed from the pins 47 in this manner.

The last major functional component of the multi-pin system 10 of the present invention is the central control unit 24. The central control unit 24 is generally a programmable controller that coordinates all movements and actuations of the system. preferably, the central control unit 24 controlling the system includes a programmable logic controller (PLC) with a human machine interface (HMI) and a position controller, which may be provided directly on the frame 12 or be remotely located. The control system not only handles the positioning task of moving the multi-pin head 46 to selected regions or zones within a selected micro-plate, it also provides the operator with the option to select a user defined combination of pins 47 for the process. Execution of all sub-processes can also be initiated individually or the entire magnetic separation process can be executed via the control system 24. All required user parameters/specifications for each the above mentioned processes are defined by the operator via the HMI.

In a preferred embodiment, the control system 24 is a Programmable Logic Controller (PSI Modular) together with a Front End display unit (FED-120C) as the HMI, supplied by Festo Corporation of Hauppauge, N.Y. The PSI programmable logic controller communicates over a serial interface with a position controller (Festo SPC200), transferring the positioning data which controls the stepper motors. The Festo SPC200 is a modular position controller capable of both servo pneumatic control and stepper motor control. Three stepper motor cards are employed in the controller and the three axis system operates in open loop mode (without encoder feedback).

All operator settings are specified at the HMI device. The settings include specifying the x, y and z coordinates for a specific movement, a homing sequence, a setup menu where the number of cycles, combinatorial selection of tips, zones of the micro-plate to be used and the micro-plate selection. Other functions include a jogging function and an option to reset the system to default/factory settings.

Figure 11:
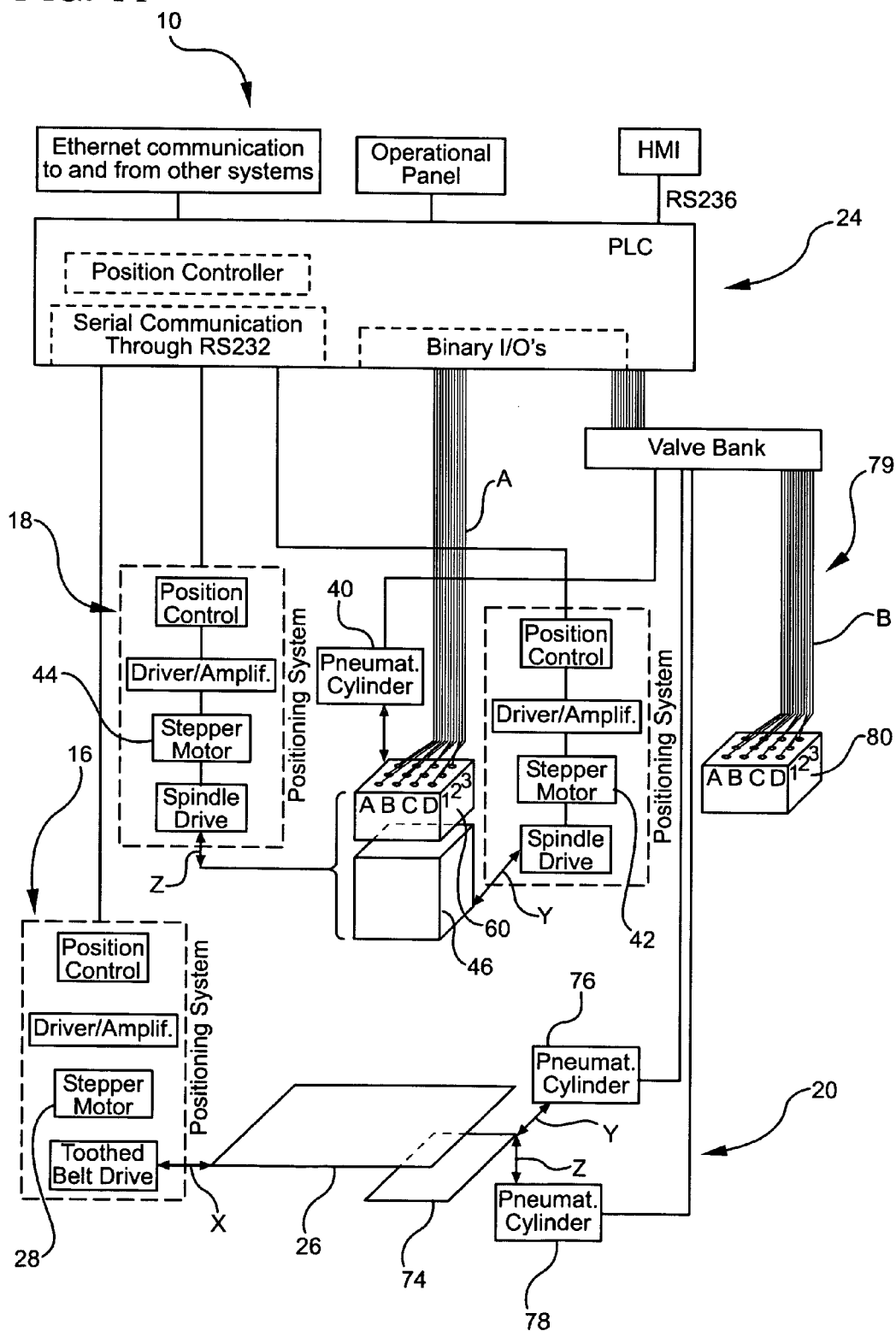
FIG. 11 is a block diagram of the overall system formed in accordance with the present invention.
Figure 13:
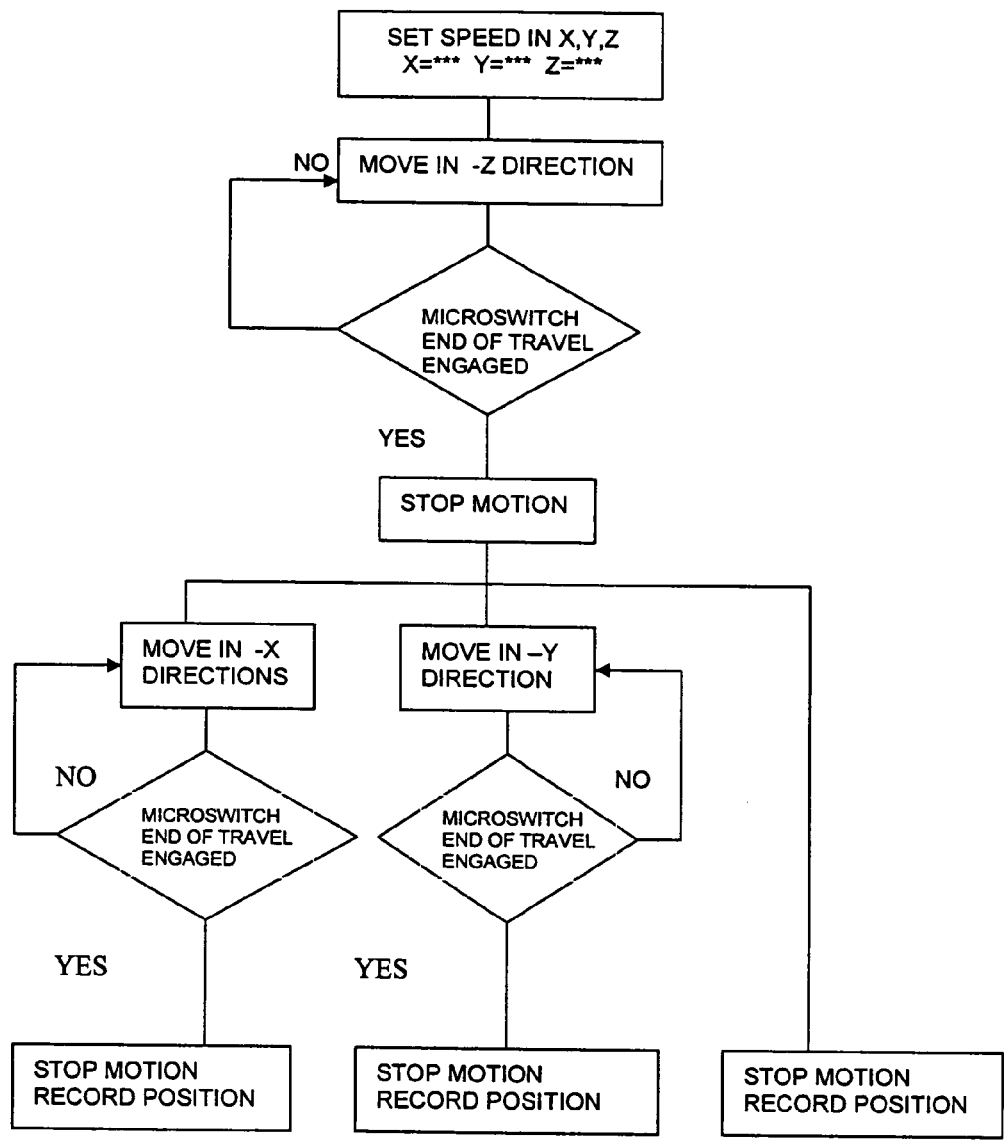
FIG. 13 is a flow chart of the homing procedure.

Referring now to FIG. 11, which is a block diagram of the overall system 10, and additionally to FIGS. 12a and 12b, which is an operational flow chart of the overall system, operation of the pin system will be described in further detail. On power up of the system 10, the operator is prompted to initialize (execute a reference run) the axes prior to proceeding with the main menu/entering of process parameters. Referring additionally to FIG. 13, the "homing process" involves the stepper motor controller executing a reference run on all three axes at a user defined speed. Limit or overtravel sensors 29 may be mounted on each end of each axis for use in the homing process. (See FIGS. 2 and 4.) Thus, "Home" can be defined by the limit switch 29 at the end of the axes where the motor is mounted.

Figure 14:
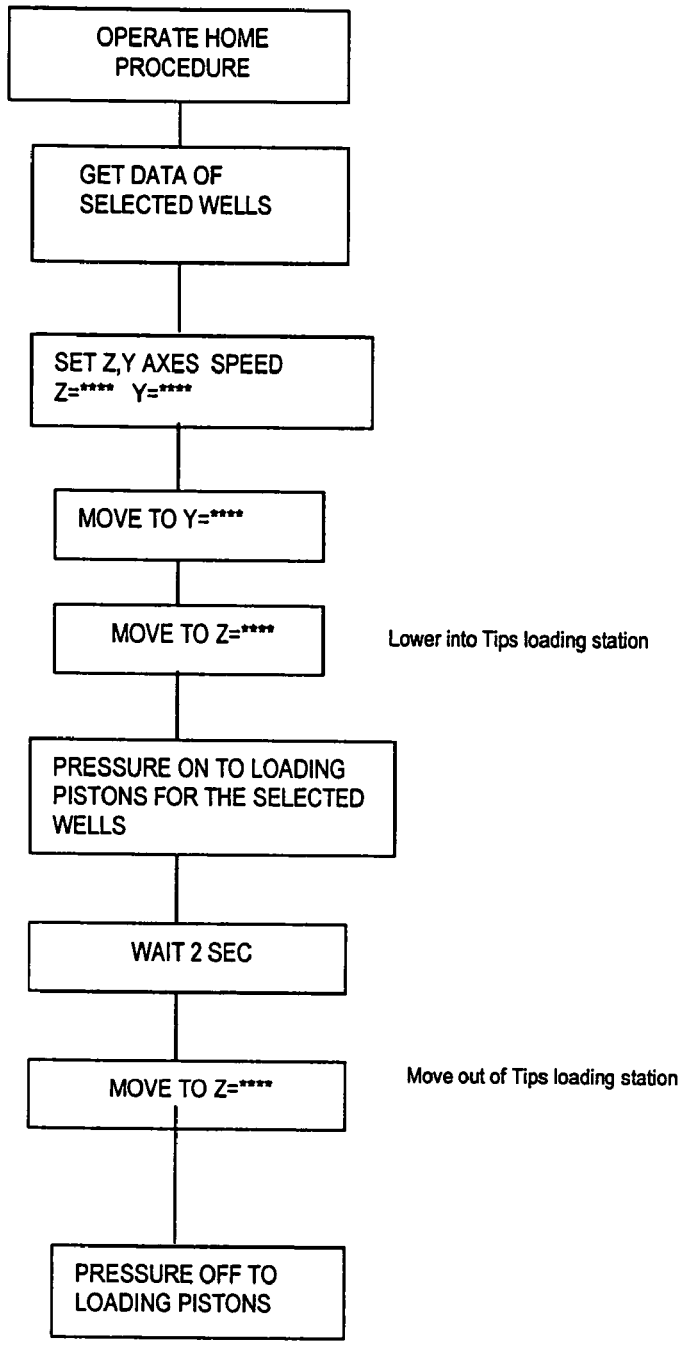
FIG. 14 is a flow chart of the tips loading procedure.

Referring to FIG. 14, the next sub-process that is executed in a complete separation cycle is the "tip loading process." The axes are preferably brought to their home positions prior to executing the loading of tips 84 on the pins 47. As mentioned above, the pins 47 to be loaded with tips will be specified on the HMI via the tip selection pad 92. The position coordinates of the tip loading station 79 are preferably preset and can not be changed by the operator. Once the multi pin head 46 is in position and lowered into the tip loading station 79, the tip loading pistons 91 (which initially reside at the bottom 88 of the bores 82 of the manifold block 80) corresponding to the selected pins are extended thereby loading the tips 84 firmly onto the selected pins 47. The multi-pin array 46 of the primary magnet unit 18 is then raised to its home position and the tip loading pistons 91 are retracted.

Figure 15:
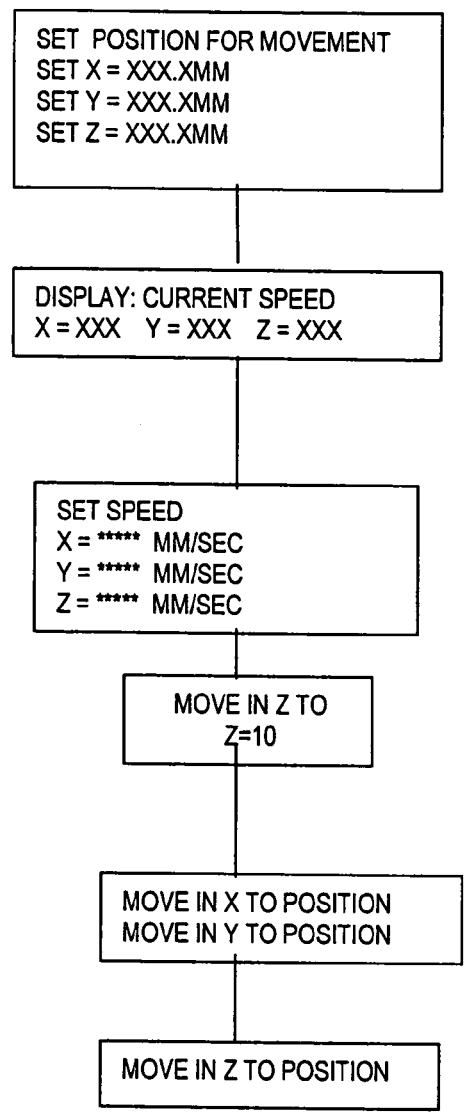
FIG. 15 is a flow chart of the xyz positioning procedure.

Once the tips 84 are loaded, the multi-pin head 46 will move to a specified zone on a selected micro-plate 30 by executing an xyz positioning sequence, as shown in FIG. 15, wherein the xy positioning is based on "Zone" or "Well" positions. Specifically, the micro-plate 30 is divided into a plurality of zones, each zone having a well array corresponding to the size and arrangement of the pin array 46. Thus, in the embodiment shown in the drawings, the micro-well plate 30 will be divided into a plurality of zones, wherein each zone has a 4×3 matrix of wells and an assigned location.

Prior to positioning, the operator is preferably prompted to select the tray number, zone within that tray and the corresponding wells within the zone. Based on the selected tray, zone and wells, the positioning coordinates for the x and y axis are calculated by the PLC and transferred to the position controller via the serial interface. Initializing the positioning task and coordinating the movements (interlocks) between the axes is achieved by using handshaking signals (Start/Motion complete) and discrete I/O signals of the position controller. Positioning instructions refer to the positions transferred to the position controller over the serial interface and instructions to be executed are selected using the discrete I/O (Record select mode).

The z-axis positioning of the multi-pin head 46 can be specified in millimeters (mm) by the operator as the well depth can differ from different micro-plate suppliers. Liquid levels can also vary within the wells. Moreover, the speeds for each axis can also be specified by the operator in mm/s.

The execution of the movement starts with the multi-pin head 46 retracting in the z-direction to a predefined (factory preset) position to ensure the pins 47 will clear the surface of the micro-plate 30. The micro-well drive unit 16 then positions the micro-well plate 30 in the x-direction while the y-motor 42 of the primary magnet unit 18 positions the multi-pin head 46 in the y-direction. The same positioning sequence applies to both moving the multi-pin head 46 to a sample micro-well tray and moving the head to a separate washing liquid tray. The sequences are preferably interlocked by the handshaking signals of the position controller.

Figure 16A:
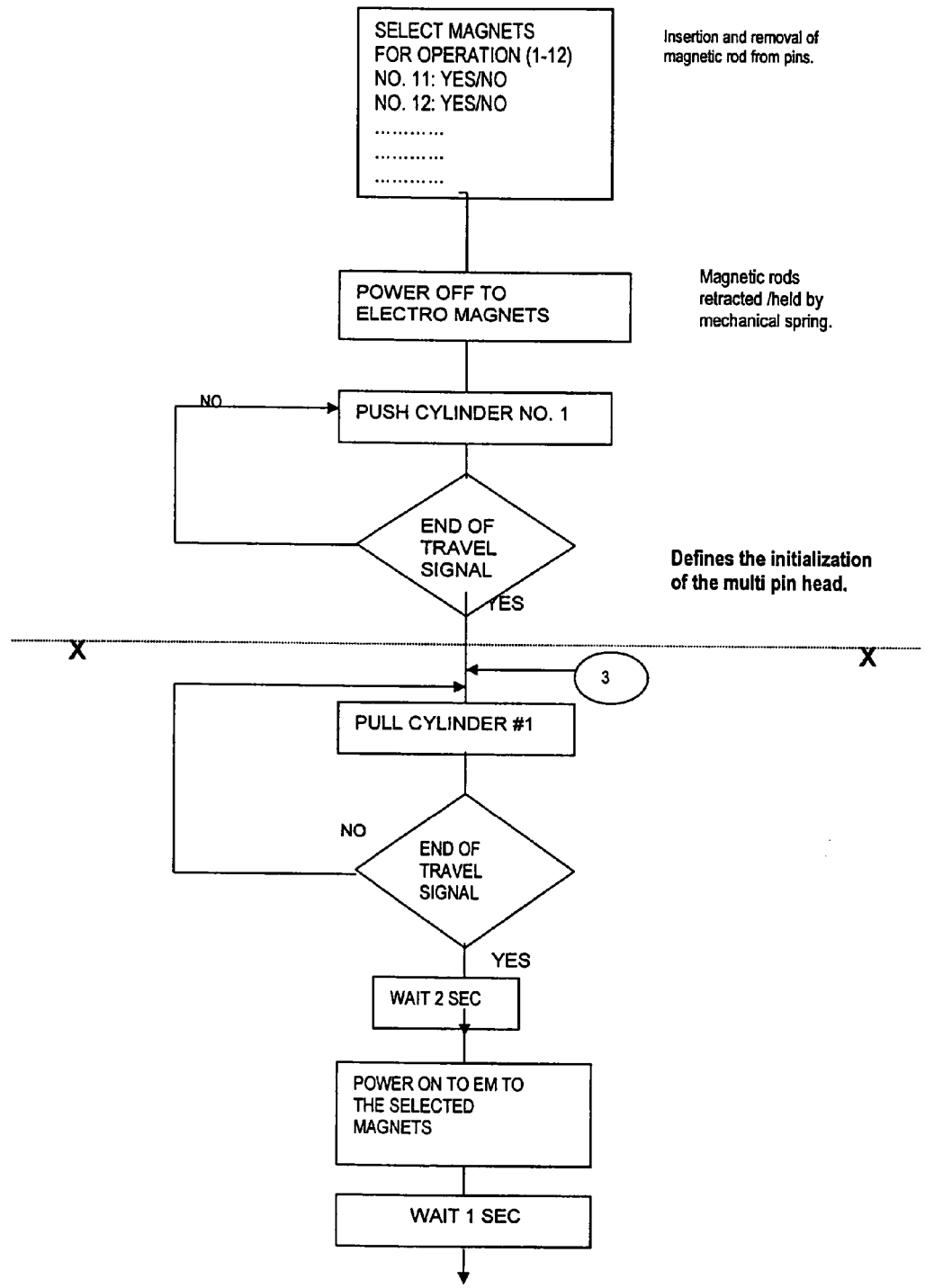
FIGS. 16a and 16b is a flow chart of the push/pull magnet procedure.
Figure 16B:
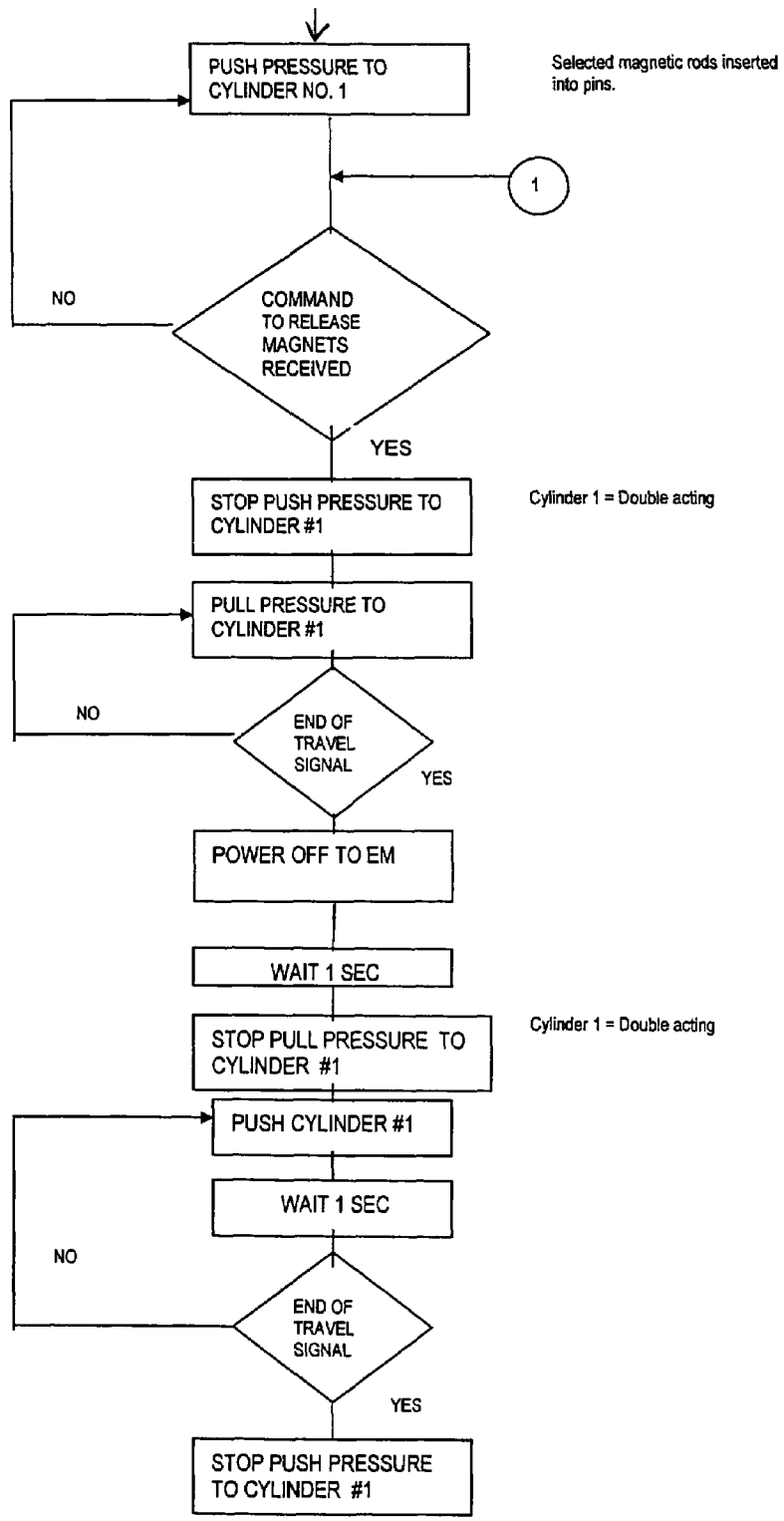

Referring now additionally to FIGS. 16a and 16b, the next sequence, termed the "push/pull magnet sequence" essentially involves the selection of pins 47 within the multi-pin head 46 and the insertion of the selected magnetic rods 66 into these pins by the multi-pin actuator 40. As described above, and shown in FIG. 5, in the preferred embodiment, this process is achieved by the actuation of the double acting cylinder 62 which lifts and lowers an actuator plate 60 having an array of electromagnets 61 provided thereon. The default state of the multi-pin head would be with the cylinder extended where the electromagnet array is held away from the mechanical coils 71 which hold the magnetic rods 66 in their default position.

The push/pull process is activated by retracting the double acting cylinder 62, raising the electromagnet array 61 towards the supporting piston housing 69. The selected electromagnets 61 draw their respective ferromagnetic pistons 65 out of the piston housing 69 (overcoming the mechanical spring force which keeps the magnetic rods 66 in their home position) and the rods are then inserted into the hollow pins 47. The double acting cylinder 62 is also preferably fitted with two limit switches (not shown).

Figure 17A:
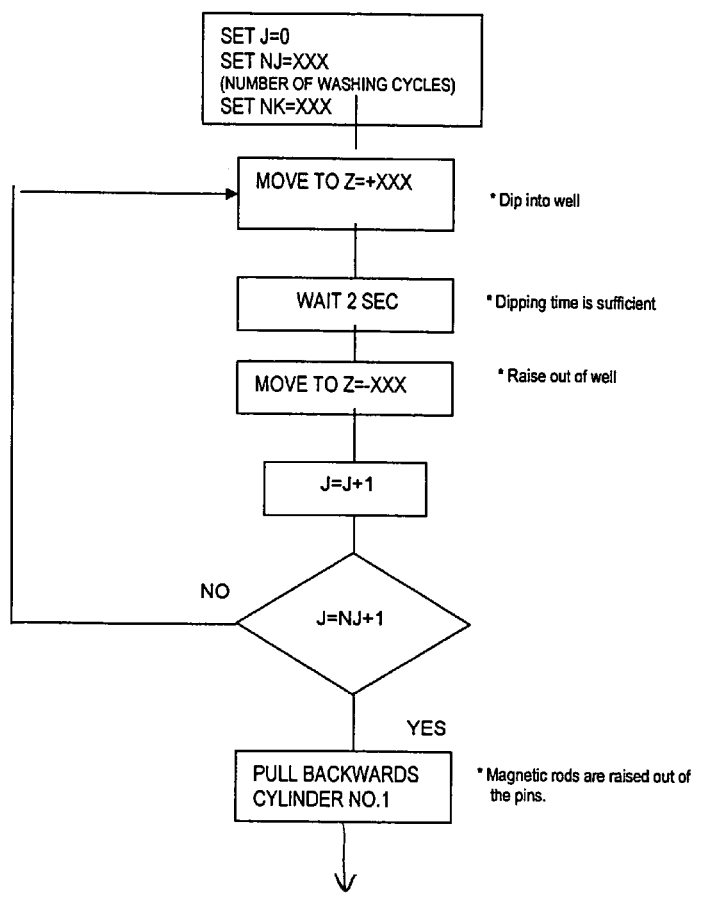
FIGS. 17a and 17b is a flow chart of the washing procedure.
Figure 17B:
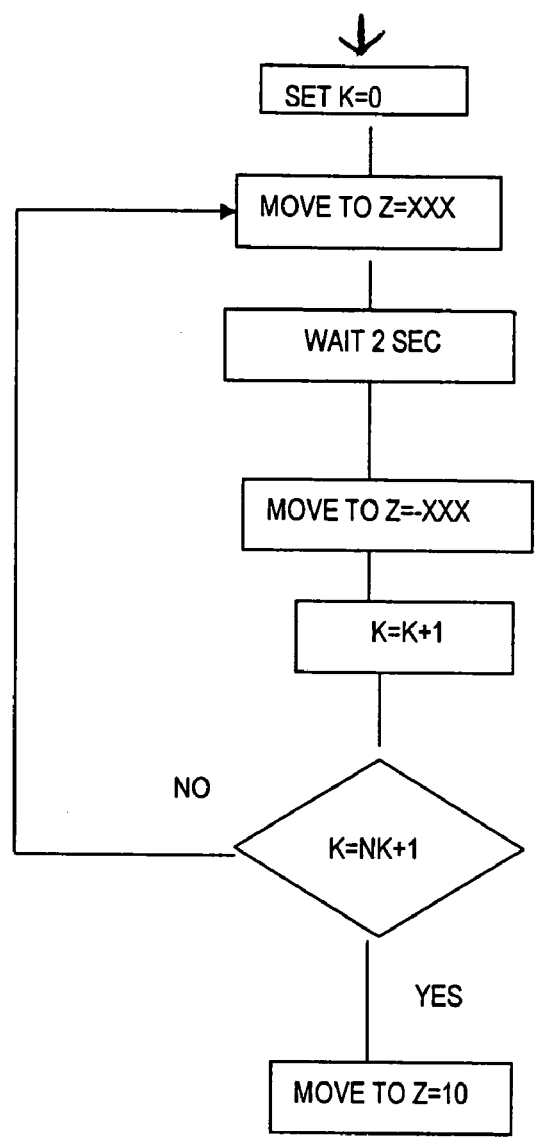

Referring now additionally to FIGS. 17a and 17b, the "washing procedure" generally involves the moving of the multi-pin head, with magnetic particles attached to the selected tips, to a target zone of the micro-well plate or to another plate altogether. Briefly, the multi-pin head 46 is moved in the z-direction to repeatedly dip and raise the pin tips 49, 84 into and out of the micro-wells containing a "washing" fluid therein. At the same time, the magnetic rods 66 are retracted from inside the pins 47, thereby removing the magnetic force from the tips. In this manner, the magnetic particles are released from the ends of the pins 47 and are captured by the "washing" fluid within the micro-wells.

Figure 18A:
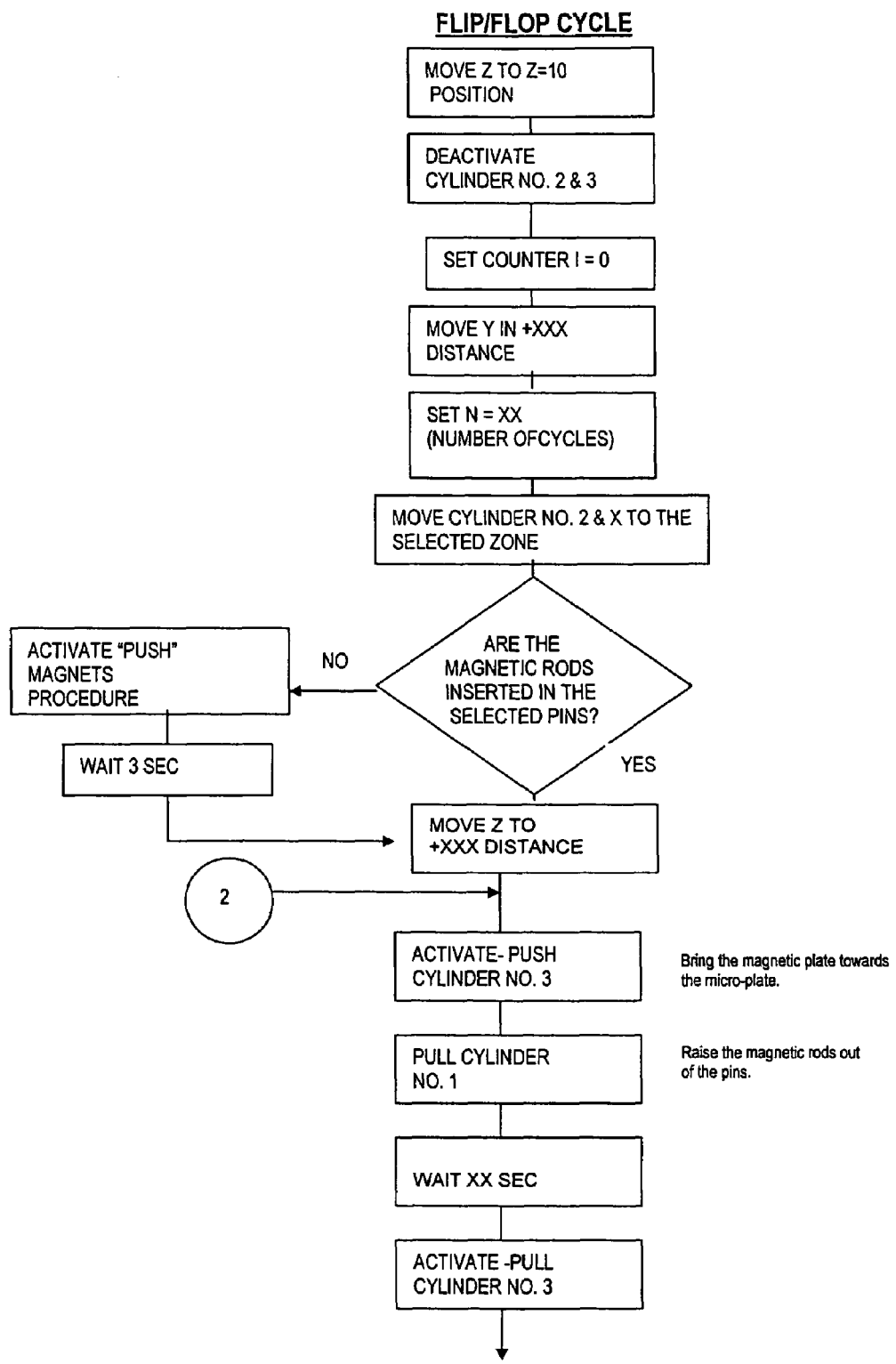
FIGS. 18a and 18b is a flow chart of the flip/flop cycle.
Figure 18B:
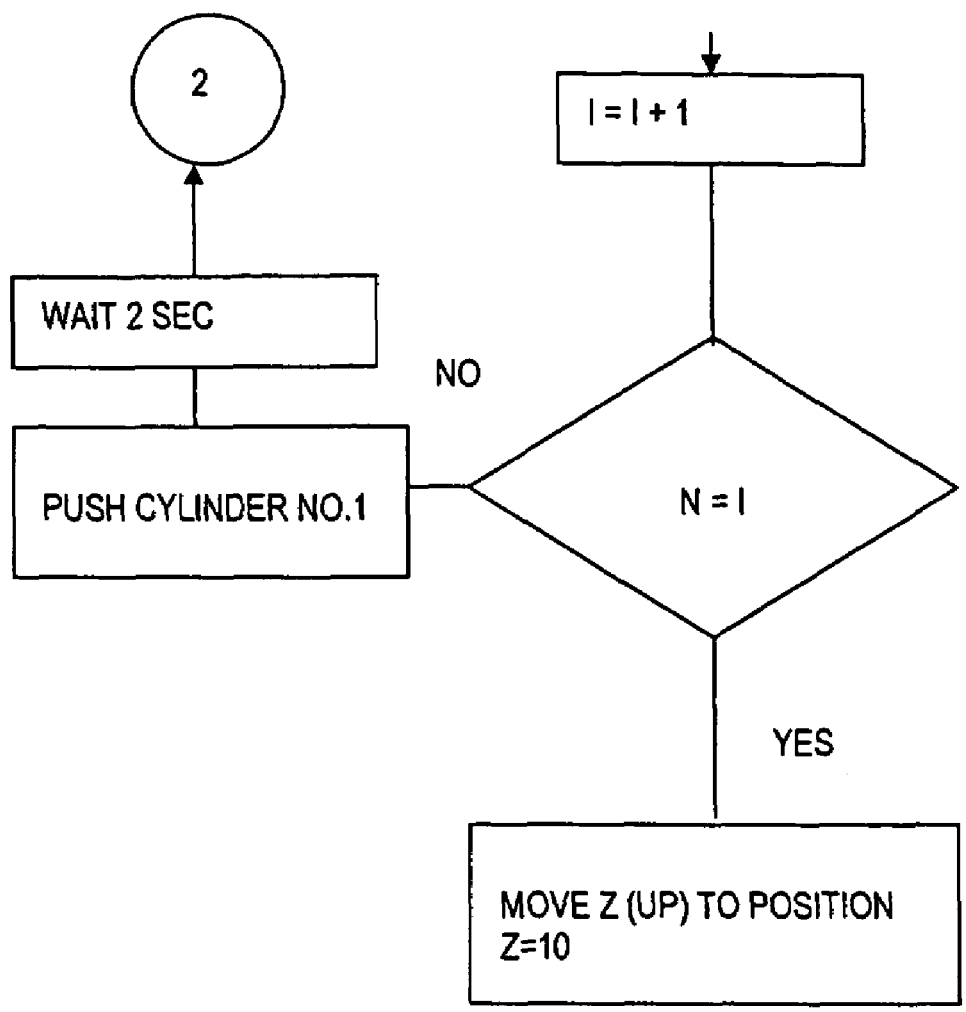

As discussed above, both the "push/pull" sequence and the "washing procedure" may further involve a "flip/flop cycle" which makes use of the secondary magnet unit 20. Referring now additionally to FIGS. 18a and 18b, the "flip/flop cycle" generally involves coordinated movement and actuation of the primary magnet unit 18 and the secondary magnet unit 20 from above and below the micro-well tray 30. Essentially, the secondary magnet unit 20 is brought up to the micro-well tray 30 as the primary magnet unit 18 is lifted upwardly away from the tray so that the magnets of the secondary magnet unit will help retain magnetic particles in the micro-well trays that have not been selected. As also discussed above, this process is further enhanced when the secondary magnet unit 20 is provided with "combinatorial" capabilities, wherein individual secondary magnets can be independently actuated, as described above and shown in FIG. 10.

Figure 19:
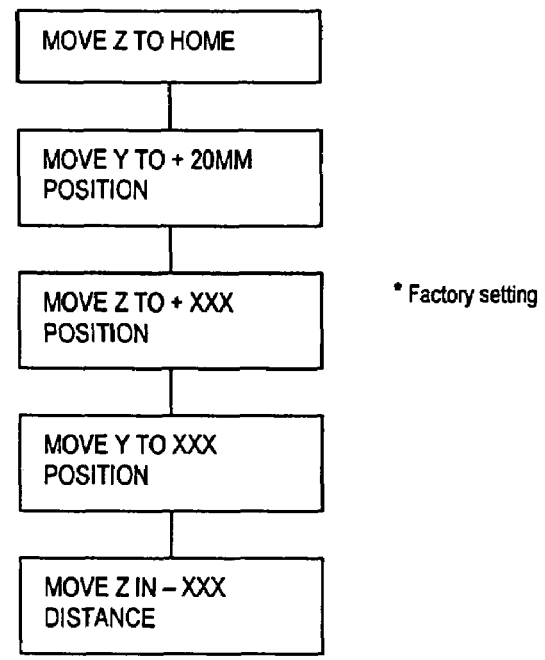
FIG. 19 is a flow chart of the tip discard procedure.

Once a magnet separation process is complete, the tip discard procedure can be initiated, as shown in FIG. 19. As discussed above, the tip discard procedure generally involves moving the multi-pin head 46 into engagement with the tip removal fork 94 and elevating the head in the z-direction, whereby the fork will disengage the tips from the pins to be captured in the tip receptacle 98.

As a result of the present invention, a three axis transfer device control system is provided which enables the separation and transfer of any desired combination of samples with the advantage of executing multiple tests in a single run. The design offers significant advantages in addition to the accuracy of movement, reliability, reduction in cost of the process and efficiency. The flexibility of the system due to the several modes of operation (combinatorial functionality) allows the system to be operated as a fixed transfer device with the capability of breaking the array into smaller sub-arrays.

While the system of the present invention has been primarily described herein as a system utilizing magnetic forces for attracting and releasing magnetic particles, those skilled in the art will appreciate that the three axis coordinate control system of the present invention may also be employed to control movement of an array of pipettes or other transferring devices to transfer samples from one or more source vessels to one or more target vessels using known techniques. Such a device is intended to come within the scope of the invention. In particular, as mentioned herein, the system may simply include a vessel drive unit including a translatable support plate for supporting the source vessel and the target vessel thereon and a support plate drive for reciprocally translating the support plate in an x-direction. Also, in this case, the primary magnet unit would simply be termed a primary transfer unit and would include at least one transfer device.

Although the preferred embodiments of the present invention have been described with reference to the accompanying drawing, it is to be understood that the invention is not limited to those precise embodiments, and that other changes and modifications may be made by one skilled in the art without departing from the scope or spirit of the invention.

What is claimed is:

1. A control system for transferring a sample from a source vessel to a target vessel, the control system comprising:
a vessel unit including a support plate for supporting the source vessel and the target vessel thereon;
a primary transfer unit including at least one transfer device for transferring the sample from the source vessel to the target vessel, said primary transfer unit including a primary magnet unit and said transfer device uses a magnetic force to attract the sample thereto, and wherein said transfer device further includes a hollow pin body terminating at a tip and a magnet slidably disposed within said hollow pin body, and said primary magnet unit further comprises a magnet actuator system for driving said magnet to move from a first position adjacent said tip, wherein said magnet applies said magnetic force through said tip, to a second position away from said tip, wherein said magnetic force is removed from said tip;
an x-axis drive adapted to reciprocally translate one of said support plate and said transfer device in an x-direction;

a y-axis drive adapted to reciprocally translate one of said support plate and said transfer device in a y-direction;

a z-axis drive adapted to reciprocally translate one of said support plate and said transfer device in a z-direction, said x, y and z directions defining a three axis Cartesian coordinate system; and a control unit for controlling said x, y and z drives, wherein said magnet actuator system comprises:

an actuator plate having at least one individually activated electromagnet disposed thereon;

an actuator plate drive for reciprocally translating said actuator plate; and an actuator rod having a distal end connected to said magnet in said hollow pin body, said actuator rod including a ferromagnetic piston portion engageable with said electromagnet when said electromagnetic is activated for moving said magnet from said first position to said second position upon translation of said actuator plate.

2. A control system as defined in claim 1, wherein said primary magnet unit comprises an array of said pins and wherein said actuator system includes an array of electromagnets and actuator rods matching in number and arrangement with said pin array and wherein each pin of said pin array includes a magnet slidably disposed in a hollow pin body thereof and connected with a respective actuator rod.

3. A control system as defined in claim 1, wherein said actuator rod comprises a flexible cable.

4. A control system as defined in claim 1, wherein said actuator system further comprises a piston housing spaced from said actuator plate, said piston housing including a tension spring connected to said ferromagnetic piston portion of said actuator rod, for biasing said piston portion toward said piston housing.

5. A control system as defined in claim 1, wherein said magnet actuator system comprises:

an actuator rod having a proximal end and a distal end, said distal end being connected to said magnet in said hollow pin body; and an individually activated rod drive connected to said proximal end of said actuator rod for moving said magnet from said first position to said second position.

6. A control system as defined in claim 1, further comprising a tip insertion unit for applying a disposable tip to said at least one transfer device of said primary transfer unit.

7. A control system as defined in claim 1, wherein said vessel drive unit is adapted for supporting at least one microwell tray having at least one of the source vessel and the target vessel defined therein.

8. A control system for transferring a sample from a source vessel to a target vessel, the control system comprising:

a vessel unit including a support plate for supporting the source vessel and the target vessel thereon;

a primary transfer unit including at least one transfer device for transferring the sample from the source vessel to the target vessel, said primary transfer unit including a primary magnet unit and said transfer device uses a magnetic force to attract the sample thereto, and wherein said transfer device further includes a hollow pin body terminating at a tip and a magnet slidably disposed within said hollow pin body, and said primary magnet unit further comprises a magnet actuator system for driving said magnet to move from a first position adjacent said tip, wherein said magnet applies said magnetic force through said tip, to a second position away from said tip, wherein said magnetic force is removed from said tip;

an x-axis drive adapted to reciprocally translate one of said support plate and said transfer device in an x-direction;

a y-axis drive adapted to reciprocally translate one of said support plate and said transfer device in a y-direction;

a z-axis drive adapted to reciprocally translate one of said support plate and said transfer device in a z-direction, said x, y and z directions defining a three axis Cartesian coordinate system; and a control unit for controlling said x, y and z drives, wherein said magnet actuator system comprises:

an actuator rod having a proximal end and a distal end, said distal end being connected to said magnet in said hollow pin body, wherein said actuator rod comprises a flexible cable; and an individually activated rod drive connected to said proximal end of said actuator rod for moving said magnet from said first position to said second position.

9. A control system for transferring a sample from a source vessel to a target vessel, the control system comprising:

a vessel unit including a support plate for supporting the source vessel and the target vessel thereon;

a primary transfer unit including at least one transfer device for transferring the sample from the source vessel to the target vessel;

an x-axis drive adapted to reciprocally translate one of said support plate and said transfer device in an x-direction;

a y-axis drive adapted to reciprocally translate one of said support plate and said transfer device in a y-direction;

a z-axis drive adapted to reciprocally translate one of said support plate and said transfer device in a z-direction, said x, y and z directions defining a three axis Cartesian coordinate system;

a control unit for controlling said x, y and z drives; and a magnet unit including at least one magnet element supported on a magnet plate, said support plate of said vessel unit being disposed between said transfer device of said primary transfer unit and said magnet element of said magnet unit.

10. A control system as defined in claim 9, wherein said magnet unit further comprises a y-axis magnet plate drive for reciprocally translating said magnet plate in the y-direction and a z-axis magnet plate drive for reciprocally translating said magnet plate in the z-direction.

11. A control system as defined in claim 9, wherein said magnet element is adapted to be selectively activated and de-activated for alternately applying and removing a magnetic field at a bottom of at least one of the source vessel and the target vessel.

12. A control system as defined in claim 11, wherein said magnet unit further comprises:

an array of magnet elements; and a magnet actuator system for selectively activating and de-activating at least one magnet element of said array.

13. A control system as defined in claim 11, wherein said magnet element comprises a magnet slidably disposed in a bore of said magnet plate, and wherein said magnet unit further comprises a magnet actuator system for driving said magnet to move from a first position adjacent said vessel support plate for applying a magnetic force to at least one of the source vessel and the target vessel, to a second position away from said vessel support plate for removing said magnetic force from said at least one of the source vessel and the target vessel.

14. A control system as defined in claim 13, wherein said magnet actuator system comprises:

an actuator plate having at least one individually activated electromagnet disposed thereon;

an actuator plate drive for reciprocally translating said actuator plate; and a magnet rod having a distal end connected to said magnet in said magnet plate, said magnet rod including a ferromagnetic piston portion engageable with said electromagnet when said electromagnet is activated for moving said magnet from said first position to said second position upon translation of said actuator plate.

15. A control system as defined in claim 14, wherein said actuator system includes an array of electromagnets and magnet rods matching in number and arrangement with said magnet element array, and wherein each magnet element of said array includes a magnet slidably disposed in a bore of said magnet plate and connected with a respective magnet rod.

16. A control system as defined in claim 14, wherein said magnet rod comprises a flexible cable.

17. A control system as defined in claim 14, wherein said magnet actuator system further comprises a piston housing spaced from said actuator plate, said piston housing including a tension spring connected to said ferromagnetic piston portion of said magnet rod, for biasing said piston portion toward said piston housing.

18. A control system as defined in claim 13, wherein said magnet actuator system comprises:

a magnet rod having a proximal end and a distal end, said distal end being connected to said magnet in said bore of said magnet plate; and an individually activated magnet rod drive connected to said proximal end of said magnet rod for moving said magnet from said first position to said second position.

19. A control system for transferring a sample from a source vessel to a target vessel, the control system comprising:

a vessel unit including a support plate for supporting the source vessel and the target vessel thereon;

a primary transfer unit including at least one transfer device for transferring the sample from the source vessel to the target vessel;

an x-axis drive adapted to reciprocally translate one of said support plate and said transfer device in an x-direction;

a y-axis drive adapted to reciprocally translate one of said support plate and said transfer device in a y-direction;

a z-axis drive adapted to reciprocally translate one of said support plate and said transfer device in a z-direction, said x, y and z directions defining a three axis Cartesian coordinate system;

a control unit for controlling said x, y and z drives; and a tip insertion unit for applying a disposable tip to said at least one transfer device of said primary transfer unit, wherein said tip insertion unit comprises:

a block having a bore formed therein, said bore having a proximal end and a distal end, said proximal end being sized to receive a disposable tip for application to said transfer device; and a pressure source connected to said distal end of said bore for applying a pressure in said bore for forcing the disposable tip out of said bore.

20. A control system as defined in claim 19, wherein said block further includes a piston slidably received within said bore, said piston being driven by said pressure applied by said pressure source to force the disposable tip out of said bore.

21. A control system as defined in claim 19, further comprising a tip removal unit for removing a disposable tip from said at least one transfer device of said primary transfer unit.

22. A control system as defined in claim 21, wherein said tip removal unit comprises a fork defined by at least one channel having a width corresponding to a diameter of said transfer device, said channel being adapted to engage a disposable tip of said transfer device when said transfer device is brought into said channel.

23. A system for transferring a sample from a source vessel to a target vessel, the system comprising:

a transfer device having a hollow body terminating at a tip and an actuating element movably disposed in said hollow body between a first position adjacent said tip and a second position away from said tip, said movement of said actuating element causing a sample in proximity to said transfer device to be alternately collected and released from said transfer device;

an actuator plate having at least one individually activated electromagnet disposed thereon;

an actuator plate drive for reciprocally translating said actuator plate; and an actuator rod having a distal end connected to said actuating element in said hollow body of said transfer device, said actuator rod including a ferromagnetic piston portion engageable with said electromagnet when said electromagnetic is activated for moving said actuating element from said first position to said second position upon translation of said actuator plate.

24. A system as defined in claim 23, wherein said actuating element of said transfer device is a magnet slidably disposed within said hollow body between said first position and said second position, wherein a magnetic force is applied at said tip when said magnet is in said first position, and wherein said magnetic force is removed from said tip when said magnet is in said second position for alternately collecting and releasing samples from said transfer device.

25. A system as defined in claim 23, wherein said actuator rod comprises a flexible cable.

26. A system as defined in claim 23, further comprising a piston housing spaced from said actuator plate, said piston housing including a tension spring connected to said ferromagnetic piston portion of said actuator rod, for biasing said piston portion toward said piston housing.

* * * * *